United States Patent [19]

Berger et al.

[11] 4,349,678
[45] Sep. 14, 1982

[54] OCTAHYDRO-2-METHYL-ISOQUINOLINE-6,8-DIONE

[75] Inventors: Leo Berger, Montclair; Gary L. Olson, Westfield, both of N.J.

[73] Assignee: Hoffmann-La Roche Inc., Nutley, N.J.

[21] Appl. No.: 215,941

[22] Filed: Dec. 12, 1980

Related U.S. Application Data

[60] Division of Ser. No. 73,813, Sep. 10, 1979, abandoned, which is a continuation-in-part of Ser. No. 950,947, Oct. 13, 1978, abandoned.

[51] Int. Cl.³ .............................................. C07D 217/24
[52] U.S. Cl. ..................................... 546/150; 424/258; 544/126; 544/361; 546/84; 260/326.14 R; 564/154
[58] Field of Search ........................................ 546/150

[56] References Cited

U.S. PATENT DOCUMENTS 3,459,755 8/1969 Mathison et al. .................. 546/150

FOREIGN PATENT DOCUMENTS 50-43546 4/1975 Japan.
51-118799 10/1976 Japan.

OTHER PUBLICATIONS

Naruto, et al., "Chem. Pharm. Bul.," Japan, vol. 23, 1975, pp. 3184–3188.
LeGoffie, et al., "Chemical Abstracts," vol. 71, 1978, col. 78773e.
Kimoto, et al., "Chem. Pharm. Bull.," Japan, vol. 10, No. 5, 1962, pp. 362–365.
Berger, et al., "Chemical Abstracts," vol. 93, 1980, col. 239390j.

*Primary Examiner*—Donald G. Daus
*Assistant Examiner*—James H. Turnipseed
*Attorney, Agent, or Firm*—Jon S. Saxe; Bernard S. Leon; William G. Isgro

[57] ABSTRACT

Neuroleptically active octahydro-1H-pyrrolo[2,3-g]isoquinolines of the formula

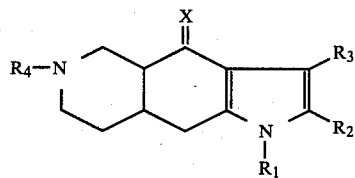

wherein $R_1$, $R_2$, $R_3$, $R_4$ and X are as hereinafter set forth, are described.

1 Claim, No Drawings

OCTAHYDRO-2-METHYL-ISOQUINOLINE-6,8-DIONE

CROSS-REFERENCE TO RELATED APPLICATIONS

This is a division of application Ser. No. 073,813, filed Sept. 10, 1979, now abandoned, which in turn is a continuation-in-part of Ser. No. 950,947, filed Oct. 13, 1978, and now abandoned.

BRIEF SUMMARY OF THE INVENTION

The invention relates to octahydro-1H-pyrrolo[2,3-g]isoquinolines of the formula:

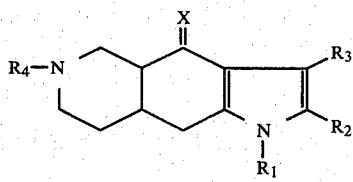

wherein $R_1$ is hydrogen, alkyl, alkanoyl, aroyl or aralkyl; $R_2$ and $R_3$, independently, are hydrogen, alkyl, cycloalkyl, alkenyl, acyl, aryl, or aralkyl; $R_4$ is hydrogen, alkyl, hydroxyalkyl, phenylhydroxyalkyl, halophenyl-hydroxyalkyl, alkylphenyl-hydroxyalkyl, alkoxyphenylhydroxyalkyl, alkoxyalkyl, aryloxy-hydroxyalkyl, alkoxyhydroxyalkyl, acyloxyalkyl, arylcarbonylalkyl, alkoxycarbonylalkyl, aralkyl, alkenyl, alkyl-cycloalkyl, alkynyl, thienyl-alkyl, furyl-alkyl, arylcarboxamidoalkyl, acylalkyl, cyclic-alkyloxoalkyl, cyclic-alkylhydroxyalkyl, alkenyloxyalkyl, aralkenyl, aryloxyalkyl, N-alkyl-pyrrolidinylalkyl, trifluoroalkyl of 2 to 6 carbon atoms, aryl-N-imidazolonylalkyl, or

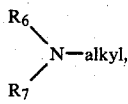

wherein $R_6$ and $R_7$, independently, are hydrogen or alkyl, or taken together with the nitrogen, are a 5- or 6-membered heterocyclic ring; and X is O or S, and their pharmaceutically acceptable acid addition salts.

In yet another aspect, the invention relates to intermediates of the formulas:

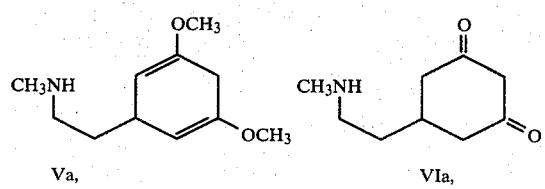

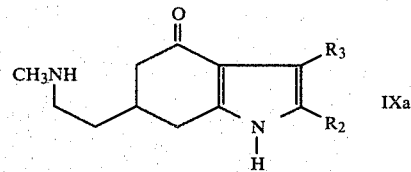

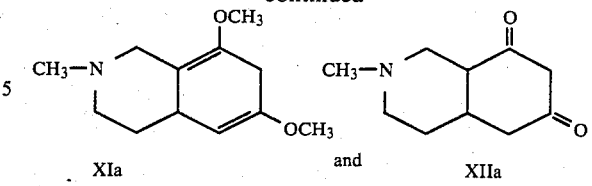

DETAILED DESCRIPTION OF THE INVENTION

The invention relates to octahydro-1H-pyrrolo[2,3-g]isoquinolines of the formula:

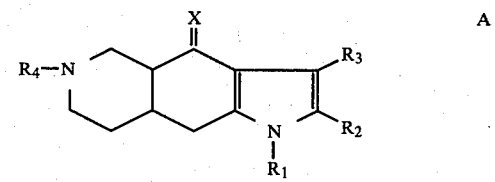

wherein $R_1$ is hydrogen, alkyl, alkanoyl, aroyl or aralkyl; $R_2$ and $R_3$, independently, are hydrogen, alkyl, cycloalkyl, alkenyl, acyl, aryl or aralkyl; $R_4$ is hydrogen, alkyl, hydroxyalkyl, phenyl-hydroxyalkyl, halophenyl-hydroxyalkyl, alkylphenyl-hydroxyalkyl, alkoxyphenyl-hydroxyalkyl, alkoxyalkyl, aryloxyhydroxyalkyl, alkoxy-hydroxyalkyl, acyloxyalkyl, arylcarbonylalkyl, alkoxycarbonylalkyl, aralkyl, alkenyl, alkyl-cycloalkyl, alkynyl, thienyl-alkyl, furyl-alkyl, arylcarboxamidoalkyl, acylalkyl, cyclic-alkyloxoalkyl, cyclic-alkylhydroxyalkyl, alkenyloxyalkyl, aralkenyl, aryloxyalkyl, N-alkyl-pyrrolidinylalkyl, trifluoroalkyl of 2 to 6 carbon atoms, aryl-N-imidazolonylalkyl, or

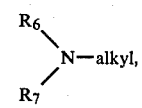

wherein $R_6$ and $R_7$, independently, are hydrogen or alkyl, or taken together with the nitrogen, are a 5- or 6-membered heterocyclic ring; and X is O or S, and pharmaceutically acceptable acid addition salts thereof.

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "alkoxy" preferably denotes "lower alkoxy", which denotes an alkyl ether group in which the lower alkyl group is as described above, for example, methoxy, ethoxy, propoxy, pentoxy, and the like. The term "alkenyl" preferably denotes "lower alkenyl", which denotes a straight or branched chain unsaturated hydrocarbon containing 2 to 7 carbon atoms, for example, vinyl, allyl, and the like. The term "alkynyl" preferably denotes "lower alkynyl", which denotes a straight or branched chain unsaturated hydrocarbon containing 2 to 7 carbon atoms, for example, ethynyl, propargyl, methylbutynyl, and the like. The term "halogen" or "halo" denotes all the halogens, i.e., bromine, chlorine, fluorine, and iodine. The term "trifluoroalkyl of 2 to 6 carbon atoms" preferably denotes 2,2,2-trifluoroethyl and the like. The term "aryl" denotes phenyl or phenyl bearing one or more substituents selected from the group consisting of halogen, trifluoromethyl, lower alkyl, lower alkoxy, nitro, amino, lower alkylamino, and di-lower alkylamino. The term "aralkyl" preferably denotes benzyl and the like. The term "aryloxy" denotes an aryl ether group in which the aryl group is as described above, for example, phenoxy and the like. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, such as benzoyl and the like. The term "acyloxy" denotes an "alkanoyloxy" group derived from an aliphatic carboxylic acid of 1 to 7 carbon atoms, for example, formyloxy, acetoxy, propionyloxy, and the like; and an "aroyloxy" group derived from an aromatic carboxylic acid, such as benzoyloxy and the like. The term "cyclic-alkyl" denotes a cycloalkyl group of 3 to 6 carbon atoms, that is, cyclopropyl, cyclobutyl, cyclopentyl and cyclohexyl, or a bicycloalkyl group such as bornyl or a tricycloalkyl group such as adamantyl. The 5-membered or 6-membered heterocyclic ring is derived from a saturated heterocyclic compound comprising one or two nitrogen atoms or one nitrogen atom and one oxygen atom where the second nitrogen atom may be substituted by alkyl or hydroxyalkyl, for example, morpholino, N-methyl-piperazino, piperazino, pyrrolidino, and the like.

Preferred compounds of formula A are those wherein $R_1$ is hydrogen, $R_2$ and $R_3$ are alkyl; $R_4$ is alkyl, hydroxyalkyl, phenyl-hydroxyalkyl, halophenyl-hydroxyalkyl, alkoxyalkyl, aryloxyalkyl, arylcarbonylalkyl, or aralkyl; and X is O.

Most preferred compounds of formula A of the invention wherein X is O are:
3-ethyl-2,6-dimethyl-4,4a,5,6,7,8,8a,9-octahydro-4a,8a-trans-1H-pyrrolo[2,3-g]isoquinolin-4-one;
(−)-3-ethyl-2,6-dimethyl-4,4a,5,6,7,8,8a,9-octahydro-4a,8a-trans-1H-pyrrolo[2,3-g]isoquinolin-4-one;
(−)-3-ethyl-2,6-dimethyl-4,4a,5,6,7,8,8a,9-octahydro-4a,8a-trans-1H-pyrrolo[2,3-g]isoquinolin-4-one, hydrochloride, 0.25 molar hydrate;
2-methyl-3-ethyl-6-(2-hydroxy-2-phenylethyl)-4,4a,5,6,7,8,8a,9-octahydro-4a,8a-trans-1H-pyrrolo[2,3-g]isoquinolin-4-one;
2,3,6-trimethyl-4,4a,5,6,7,8,8a,9-octahydro-4a,8a-trans-1H-pyrrolo[2,3-g]isoquinolin-4-one;
2,3,6-trimethyl-4,4a,5,6,7,8,8a,9-octahydro-4a,8a-trans-1H-pyrrolo[2,3-g]isoquinolin-4-one, hydrochloride;
2-methyl-3-ethyl-6-benzyl-4,4a,5,6,7,8,8a,9-octahydro-4a,8a-trans-1H-pyrrolo[2,3-g]isoquinolin-4-one;
2-methyl-3-ethyl-6-benzyl-4,4a,5,6,7,8,8a,9-octahydro-4a,8a-trans-1H-pyrrolo[2,3-g]isoquinolin-4-one, hydrochloride;
2-methy-3-ethyl-6-(2-phenylethyl)-4,4a,5,6,7,8,8a,9-octahydro-4a,8a-trans-1H-pyrrolo[2,3-g]isoquinolin-4-one;
2-methyl-3-ethyl-6-(2-ethoxyethyl)-4,4a,5,6,7,8,8a,9-octahydro-4a,8a-trans-1H-pyrrolo[2,3-g]isoquinolin-4-one;
2-methyl-3-ethyl-6-(2-ethoxyethyl)-4,4a,5,6,7,8,8a,9-octahydro-4a,8a-trans-1H-pyrrolo[2,3-g]isoquinolin-4-one, hydrochloride;
2-methyl-3-ethyl-6-[4-(4-fluorophenyl)-4-oxobutyl]-4,4a,5,6,7,8,8a,9-octahydro-4a,8a-trans-1H-pyrrolo[2,3-g]isoquinolin-4-one;
2-methyl-3-ethyl-6-[3-(4-fluorophenyl)-3-oxopropyl]-4,4a,5,6,7,8,8a,9-octahydro-4a,8a-trans-1H-pyrrolo[2,3-g]isoquinolin-4-one;
2-methyl-3-ethyl-6-(3-phenoxypropyl)-4,4a,5,6,7,8,8a,9-octahydro-4a,8a-trans-1H-pyrrolo[2,3-g]isoquinolin-4-one;
2-methyl-3-ethyl-6-(2-hydroxy-3-methylbutyl)-4,4a,5,6,7,8,8a,9-octahydro-4a,8a-trans-1H-pyrrolo[2,3-g]isoquinolin-4-one;
2-methyl-3-ethyl-6-(2-hydroxy-3,3-dimethylbutyl)-4,4a,5,6,7,8,8a,9-octahydro-4a,8a-trans-1H-pyrrolo[2,3-g]isoquinolin-4-one; and
2,6-dimethyl-3-ethyl-4,4a,5,6,7,8,8a,9-octahydro-4a,8a-trans-1H-pyrrolo[2,3-g]isoquinolin-4-one, hydrochoride, dihydrate.

Exemplary of the compounds of formula A wherein X is O are:
2-methyl-3-ethyl-4,4a,5,6,7,8,8a,9-octahydro-1H-pyrrolo[2,3-g]isoquinolin-4-one;
3-ethyl-2,6-dimethyl-4,4a,5,6,7,8,8a,9-octahydro-1H-pyrrolo[2,3-g]isoquinolin-4-one;
3-ethyl-1,2,6-trimethyl-4,4a,5,6,7,8,8a,9-octahydro-1H-pyrrolo[2,3-g]isoquinolin-4-one;
1-benzoyl-2,6-dimethyl-3-ethyl-4,4a,5,6,7,8,8a,9-octahydro-1H-pyrrolo[2,3-g]isoquinolin-4-one;
3-ethyl-2-methyl-6-(2-propynyl)-4,4a,5,6,7,8,8a,9-octahydro-1H-pyrrolo[2,3-g]isoquinolin-4-one;
(+)-3-ethyl-2,6-dimethyl-4,4a,5,6,7,8,8a,9-octahydro-4a,8a-trans-1H-pyrrolo[2,3-g]isoquinolin-4-one;
(+)-3-ethyl-2,6-dimethyl-4,4a,5,6,7,8,8a,9-octahydro-4a,8a-trans-1H-pyrrolo[2,3-g]isoquinolin-4-one, hydrochloride, 0.25 molar hydrate;
3,6-dimethyl-2-(2-propyl)-4,4a,5,6,7,8,8a,9-octahydro-1H-pyrrolo[2,3-g]isoquinolin-4-one, hydrochloride;
3,6-dimethyl-2-(2-propyl)-4,4a,5,6,7,8,8a,9-octahydro-1H-pyrrolo[2,3-g]isoquinolin-4-one;
2,6-dimethyl-3-butyl-4,4a,5,6,7,8,8a,9-octahydro-1H-pyrrolo[2,3-g]isoquinolin-4-one;
2-methyl-3-ethyl-6-[2-hydroxy-2-(4-chlorophenyl)ethyl]-4,4a,5,6,7,8,8a,9-octahydro-1H-pyrrolo[2,3-g]isoquinolin-4-one;
2-methyl-3-ethyl-6-(2-hydroxyethyl)-4,4a,5,6,7,8,8a,9-octahydro-1H-pyrrolo[2,3-g]isoquinolin-4-one;
2-methyl-3-ethyl-6-(2-propenyl)-4,4a,5,6,7,8,8a,9-octahydro-1H-pyrrolo[2,3-g]isoquinolin-4-one;
2-methyl-3-ethyl-6-(2-propenyl)-4,4a,5,6,7,8,8a,9-octahydro-1H-pyrrolo-[2,3-g]isoquinolin-4-one, hydrochloride, 0.5 molar hydrate;
2-methyl-3-ethyl-6-(cyclopropylmethyl)-4,4a,5,6,7,8,8a,9-octahydro-1H-pyrrolo[2,3-g]isoquinolin-4-one;
2-methyl-3-ethyl-6-(cyclopropylmethyl)-4,4a,5,6,7,8,8a,9-octahydro-1H-pyrrolo[2,3-g]isoquinolin-4-one, hydrochloride, 0.2 molar hydrate;
2,6-dimethyl-3-ethyl-1-(2,2-dimethyl-1-oxopropyl)-4,4a,5,6,7,8,8a,9-octahydro-1H-pyrrolo[2,3-g]isoquinolin-4-one;
2,6-dimethyl-3-cyclopropyl-4,4a,5,6,7,8,8a,9-octahydro-1H-pyrrolo[2,3-g]isoquinolin-4-one;
3-ethyl-2-methyl-6-(2-dimethylaminoethyl)-4,4a,5,6,7,8,8a,9-octahydro-1H-pyrrolo[2,3-g]isoquinolin-4-one;
1-benzyl-2,6-dimethyl-3-ethyl-4,4a,5,6,7,8,8a,9-octahydro-1H-pyrrolo[2,3-g]isoquinolin-4-one;
3-ethyl-2-methyl-4,4a,5,6,7,8,8a,9-octahydro-1H-pyrrolo[2,3-g]isoquinolin-4-oxo-6-acetic acid, ethyl ester;
2-benzyl-3,6-dimethyl-4,4a,5,6,7,8,8a,9-octahydro-1H-pyrrolo[2,3-g]isoquinolin-4-one;
3,6-dimethyl-2-(2-propenyl)-4,4a,5,6,7,8,8a,9-octahydro-1H-pyrrolo[2,3-g]isoquinolin-4-one;

2,6-dimethyl-3-(2-propyl)-4,4a,5,6,7,8,8a,9-octahydro-1H-pyrrolo[2,3-g]isoquinolin-4-one;
3-ethyl-2-methyl-6-[2-hydroxy-3-(4-chlorophenoxy)propyl]-4,4a,5,6,7,8,8a,9-octahydro-1H-pyrrolo[2,3-g]isoquinolin-4-one;
3,6-diethyl-2-methyl-4,4a,5,6,7,8,8a,9-octahydro-1H-pyrrolo[2,3-g]isoquinolin-4-one;
2-methyl-3-ethyl-6-propyl-4,4a,5,6,7,8,8a,9-octahydro-1H-pyrrolo[2,3-g]isoquinolin-4-one;
2-methyl-3-ethyl-6-butyl-4,4a,5,6,7,8,8a,9-octahydro-1H-pyrrolo[2,3-g]isoquinolin-4-one;
2-methyl-3-ethyl-6-pentyl-4,4a,5,6,7,8,8a,9-octahydro-1H-pyrrolo[2,3-g]isoquinolin-4-one;
3,6-dimethyl-4,4a,5,6,7,8,8a,9-octahydro-1H-pyrrolo[2,3-g]isoquinolin-4-one;
6-methyl-4,4a,5,6,7,8,8a,9-octahydro-1H-pyrrolo[2,3-g]isoquinolin-4-one;
6-benzyl-4,4a,5,6,7,8,8a,9-octahydro-1H-pyrrolo[2,3-g]isoquinolin-4-one;
2,6-dimethyl-3-propyl-4,4a,5,6,7,8,8a,9-octahydro-1H-pyrrolo[2,3-g]isoquinolin-4-one;
3-ethyl-2-methyl-6-[2-hydroxy-3-(4-t-butylphenoxy)propyl]-4,4a,5,6,7,8,8a,9-octahydro-1H-pyrrolo[2,3-g]isoquinolin-4-one;
3-ethyl-2-methyl-6-[2-hydroxy-2-(4-chloro-3-trifluoromethylphenyl)ethyl]-4,4a,5,6,7,8,8a,9-octahydro-1H-pyrrolo[2,3-g]isoquinolin-4-one;
3-ethyl-2-methyl-6-(2-hydroxy-2-adamantylethyl)-4,4a,5,6,7,8,8a,9-octahydro-1H-pyrrolo[2,3-g]isoquinolin-4-one;
3-ethyl-2-methyl-6-[2-(4-morpholino)ethyl]-4,4a,5,6,7,8,8a,9-octahydro-1H-pyrrolo[2,3-g]isoquinolin-4-one;
3-ethyl-2-methyl-6-[2-oxo-2-(4-fluorophenyl)ethyl]-4,4a,5,6,7,8,8a,9-octahydro-1H-pyrrolo[2,3-g]isoquinolin-4-one;
3-ethyl-2-methyl-6-(2-methylpropyl)-4,4a,5,6,7,8,8a,9-octahydro-1H-pyrrolo[2,3-g]isoquinolin-4-one;
3-ethyl-2-methyl-6-cyclobutylmethyl-4,4a,5,6,7,8,8a,9-octahydro-1H-pyrrolo[2,3-g]isoquinolin-4-one;
3-ethyl-2-methyl-6-hexyl-4,4a,5,6,7,8,8a,9-octahydro-1H-pyrrolo[2,3-g]isoquinolin-4-one;
3-ethyl-2-methyl-6-heptyl-4,4a,5,6,7,8,8a,9-octahydro-1H-pyrrolo[2,3-g]isoquinolin-4-one;
3-ethyl-2-methyl-6-[2-(1-pyrrolidinyl)ethyl]-4,4a,5,6,7,8,8a,9-octahydro-1H-pyrrolo[2,3-g]isoquinolin-4-one;
3-ethyl-2-methyl-6-(4-methoxy-2-phenylethyl)-4,4a,5,6,7,8,8a,9-octahydro-1H-pyrrolo[2,3-g]isoquinolin-4-one;
2,6-dimethyl-3-ethyl-1-(1-oxobutyl)-4,4a,5,6,7,8,8a,9-octahydro-1H-pyrrolo-[2,3-g]isoquinolin-4-one;
3-ethyl-2-methyl-6-(4-chloro-2-phenylethyl)-4,4a,5,6,7,8,8a,9-octahydro-1H-pyrrolo[2,3-g]isoquinolin-4-one;
2,6-dimethyl-3-propyl-4,4a,5,6,7,8,8a,9-octahydro-4a,8a-trans-1H-pyrrolo[2,3-g]isoquinolin-4-one;
2,3-dimethyl-6-(2-phenylethyl)-4,4a,5,6,7,8,8a,9-octahydro-4a,8a-trans-1H-pyrrolo[2,3-g]isoquinolin-4-one;
2,3-dimethyl-6-[4-(4-fluorophenyl)-4-oxobutyl]-4,4a,5,6,7,8,8a,9-octahydro-4a,8a-trans-1H-pyrrolo[2,3-g]isoquinolin-4-one;
3-ethyl-2-methyl-6-(2,2,2-trifluoroethyl)-4,4a,5,6,7,8,8a,9-octahydro-4a,8a-trans-1H-pyrrolo[2,3-g]isoquinolin-4-one;
2,6-dimethyl-3-ethyl-4,4a,5,6,7,8,8a,9-octahydro-4a,8a-cis-1H-pyrrolo[2,3-g]isoquinolin-4-one;

2-acetyl-3,6-dimethyl-4,4a,5,6,7,8,8a,9-octahydro-4a,8a-trans-1H-pyrrolo-[2,3-g]isoquinolin-4-one;
3-ethyl-2-methyl-6-[2-(2-thienyl)ethyl]-4,4a,5,6,7,8,8a,9-octahydro-4a,8a-trans-1H-pyrrolo[2,3-g]isoquinolin-4-one;
3-ethyl-2-methyl-6-[2-(2-furyl)ethyl]-4,4a,5,6,7,8,8a,9-octahydro-4a,8a-trans-1H-pyrrolo[2,3-g]isoquinolin-4-one; and
3-ethyl-2-methyl-6-[2-(1,3-dihydro-2(2H)-benzoimidazolonyl)ethyl]-4,4a,5,6,7,8,8a,9-octahydro-4a,8a-trans-1H-pyrrolo[2,3-g]isoquinolin-4-one.

Most preferred compounds of formula A of the invention wherein X is S are:
2-methyl-3-ethyl-6-(2-phenylethyl)-4,4a,5,6,7,8,8a,9-octahydro-4a,8a-trans-1H-pyrrolo[2,3-g]isoquinolin-4-thione;
2,6-dimethyl-3-ethyl-4,4a,5,6,7,8,8a,9-octahydro-4a,8a-trans-1H-pyrrolo[2,3-g]isoquinolin-4-thione;
2-methyl-3-ethyl-6-[4-(4-fluorophenyl)-4-oxobutyl]-4,4a,5,6,7,8,8a,9-octahydro-4a,8a-trans-1H-pyrrolo[2,3-g]isoquinolin-4-thione; and
2-methyl-3-ethyl-6-(2-hydroxy-3,3-dimethylbutyl)-4,4a,5,6,7,8,8a,9-octahydro-4a,8a-trans-1H-pyrrolo[2,3-g]isoquinolin-4-thione.

Exemplary of compounds of formula A wherein X is S are:
2-methyl-3-ethyl-6-(2-hydroxy-2-phenylethyl)-4,4a,5,6,7,8,8a,9-octahydro-4a,8a-trans-1H-pyrrolo[2,3-g]isoquinolin-4-thione;
2,3,6-trimethyl-4,4a,5,6,7,8,8a,9-octahydro-4a,8a-trans-1H-pyrrolo[2,3-g]isoquinolin-4-thione;
2-methyl-3-ethyl-6-benzyl-4,4a,5,6,7,8,8a,9-octahydro-4a,8a-trans-1H-pyrrolo-[2,3-g]isoquinolin-4-thione;
2-methyl-3-ethyl-6-(2-ethoxyethyl)-4,4a,5,6,7,8,8a,9-octahydro-4a,8a-trans-1H-pyrrolo[2,3-g]isoquinolin-4-thione;
2-methyl-3-ethyl-6-[3-(4-fluorophenyl)-3-oxopropyl]-4,4a,5,6,7,8,8a,9-octahydro-4a,8a-trans-1H-pyrrolo[2,3-g]isoquinolin-4-thione;
2-methyl-3-ethyl-6-(3-phenoxypropyl)-4,4a,5,6,7,8,8a,9-octahydro-4a,8a-trans-1H-pyrrolo[2,3-g]isoquinolin-4-thione;
2-methyl-3-ethyl-6-(2-hydroxy-3-methylbutyl)-4,4a,5,6,7,8,8a,9-octahydro-4a,8a-trans-1H-pyrrolo[2,3-g]isoquinolin-4-thione; and
2-methyl-3-ethyl-4,4a,5,6,7,8,8a,9-octahydro-1H-pyrrolo[2,3-g]isoquinolin-4-thione.

The compounds of the invention may exist as the 4a,8a-trans or 4a,8a-cis isomers or mixtures thereof; the 4a,8a-trans isomers are preferred.

The compounds of formula A of the invention, as well as the various intermediates which also form part of the invention, are prepared utilizing the process steps hereinafter illustrated and described.

More specifically, the compounds of formula A wherein X is O are characterized by the formula:

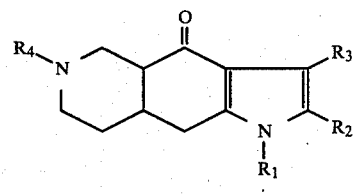

I wherein $R_1$, $R_2$, $R_3$ and $R_4$ are as hereinbefore described, and can be prepared as set forth in Schemes I, II, III and IV and further described.

FORMULA SCHEME I

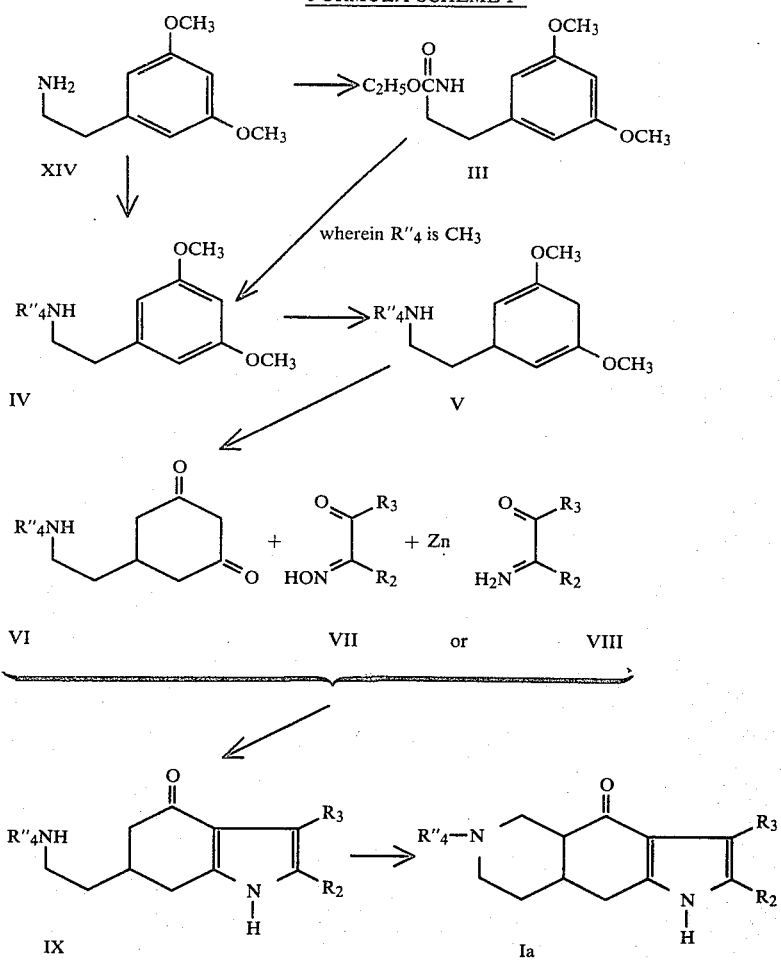

wherein $R_2$ and $R_3$ are as previously described, and $R_4''$ is alkyl, alkoxyalkyl or alkyl-cycloalkyl.

In accordance with Formula Scheme I, compounds of formula Ia wherein $R_4''$ is methyl, are prepared by reacting the primary amine of formula XIV with ethyl chloroformate to yield the urethane of formula III, which is reduced with lithium aluminum hydride to yield the N-methylamine of formula IV. In a broader aspect, the compounds of formula IV wherein $R_4''$ is alkyl, alkoxyalkyl or alkyl-cycloalkyl can be prepared by reductive alkylation of the compound of formula XIV, utilizing the corresponding aldehyde, for example, acetaldehyde, and the like, and sodium cyanoborohydride under known conditions [see, for example, R. F. Borch, J. Am. Chem. Soc., 93, 2897 (1971)]. Birch reduction of the amine of formula IV with lithium in ammonia containing t-butanol yields the dihydroamine of formula V. Other modifications of the Birch reduction may also be employed. Thus, the amine of formula IV may be reacted with an alkali metal, such as sodium, lithium, potassium or cesium, in ammonia or an amine such as methylamine or ethylamine in the presence of a lower alkanol such as ethanol, butanol, or t-butanol. The reaction is generally carried out at the boiling point of the solvent or below, for example, from $-78°$ to $15°$ C. If ammonia is used, the reaction is run at reflux. Optionally, cosolvents such as diethyl ether or tetrahydrofuran may be added.

The hydrolysis of the dihydroamine of formula V is readily accomplished by the usual methods for hydrolysis of enol ethers, for example, with aqueous acid. Exemplary of acids which may be used are hydrochloric acid, hydrobromic acid, formic acid, acetic acid, p-toluenesulfonic acid and perchloric acid. These may be used in aqueous solutions or mixed solvents. At least two equivalents of water per mole of dihydroamine and more than 1 equivalent of acid are needed. Tetrahydrofuran, benzene, diethyl ether, acetone, toluene, dioxane or acetonitrile are exemplary of the solvents which may be employed. For example, hydrolysis of the dihydroamine of formula V wherein $R_4''$ is methyl in 2 N hydrochloric acid at room temperature or above or in aqueous acetic acid at between 40° and reflux leads to the diketone of formula VI, wherein $R_4''$ is methyl.

The diketone of formula VI is condensed in a Knorr condensation to give the dihydroindolone-ethylamine of formula IX. The Knorr condensation is a well-known method for the preparation of pyrroles and the process may be used in any of the well-known modifications [see, for examplary conditions, J. M. Patterson, Synthesis, 281 (1976) and references therein]. For example, the reaction of an isonitrosoketone of formula VII in the presence of a reducing agent, for example with zinc in aqueous acetic acid or hydrochloric acid, is though to proceed via the aminocarbonyl compound of formula VIII which then condenses with the diketone of formula VI to give the product dihydroindolone-ethylamine of formula IX. Alternatively, the condensation can be carried out with an aminocarbonyl compound of formula IX or precursor thereof, such as an aminoketone hydrochloride salt, or an acetal derivative of an aminoketone or aminoaldehyde. The use of a precursor of the aminoketone or aminoaldehyde is preferred, since such substances are prone to self-condensation. They may best be utilized in situ where the aminocarbonyl component is liberated in the presence of the diketone of formula VI. The aminocarbonyl component immediately reacts to form the dihydroindolone-ethylamine of formula IX. It is not necessary to isolate the diketone of formula VI prior to carrying out the Knorr condensation since the reaction conditions employed are sufficient to hydrolyze the dihydroamine of formula V to the diketone of formula VI. The Knorr condensation is best carried out at a pH of from about pH 2 to pH 6. Much above pH 6, there is a considerable loss in yield due to the formation of self-condensation products of the aminocarbonyl compound of formula VIII.

Preferably, an isonitrosoketone of formula VII and zinc dust in aqueous acetic acid is condensed with a diketone of formula VI wherein $R_4''$ is methyl to give the product dihydroindolone-ethylamine of formula IX wherein $R_4''$ is methyl.

The Knorr condensation is preferably carried out at a temperature range of from about room temperature to reflux. The isonitrosoketones of formula VII are known compounds [see, for instance, Ferris, *J. Org. Chem.*, 24, 1726 (1959)] or can readily be prepared by nitrosation of the corresponding ketones, for example, with an alkyl nitrite, or in the case of highly acidic β-diketones or β-ketoesters, with sodium nitrite.

Exemplary of isonitrosoketones which may be used in the Knorr condensation are:
2-isonitroso-3-pentanone;
2,3-butanedione, monoxime;
2-isonitroso-4-methyl-3-pentanone;
2-isonitroso-3-hexanone;
2-isonitroso-3-heptanone;
3-isonitroso-4-methyl-2-pentanone;
2-isonitroso-1-cyclopropyl-1-propanone;
3-isonitroso-5-hexen-2-one;
cyclopropyl-2-isonitroso-1-propanone; and
3-isonitroso-4-phenyl-2-butanone.

Exemplary of aminocarbonyl precursor compounds which may be used in the Knorr condensation are:
aminoacetaldehyde dimethyl acetal; and
2-amino-3-pentanone, hydrochloride.

The amine of the formula IX is converted to the compound of the formula Ia via an intramolecular Mannich reaction. The Mannich reaction is usually performed starting with a ketone and a dialkylamine salt, for example, dimethylamine hydrochloride and formaldehyde (for example, as an aqueous solution, as paraformaldehyde or as trioxane) in an alcoholic solvent such as ethanol, at reflux. In the modification herein described, an acid addition salt of the dihydroindolone-ethylamine of formula IX is reacted with formaldehyde, added in the form of paraformaldehyde, trioxane, or as aqueous formaldehyde in a solvent. For example, a high boiling hydroxylic solvent, such as amyl alcohol, octanol, ethylene glycol or diethylene glycol monoethyl ether, a high boiling polar aprotic solvent, such as dimethylformamide, N-methylpyrrolidinone or diethylene glycol dimethyl ether; a lower boiling polar solvent, such as ethanol, butanol or 2-propanol under pressure, or a lower boiling aprotic solvent under pressure, such as dioxane or tetrahydrofuran, may be used at a temperature in the range of from about 135° to about 200° to yield the pyrrolo[2,3-g]isoquinolines of formula Ia. The reaction, especially when run at temperatures below 150° leads to a mixture of cis and trans isomers, i.e., for example, when $R_4''$ is methyl, compounds of the formulas:

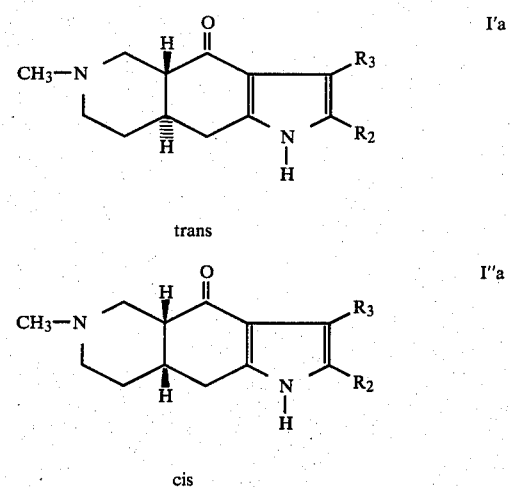

Longer heating of the reaction mixture or separate heating of the isomeric mixture of hydrochloride salts of formulas I'a and I''a, for example, in ethylene glycol at reflux for 2 hours can be used to equilibrate the cis and trans isomers to a final ratio which comprises predominantly the trans isomer, which is readily isolated by crystallization or by chromatographic separation.

Preferred is the reaction of the hydrochloride salt of the dihydroindolone-ethylamine of formula IX wherein $R_4''$ is methyl with paraformaldehyde in octanol at 180° for 2 hours, wherein the product is isolated as almost exclusively the trans isomer I'a.

FORMULA SCHEME II

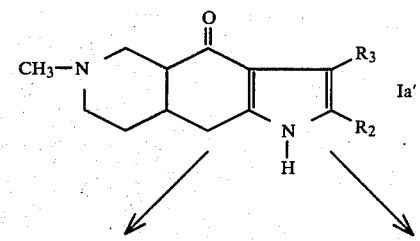

FORMULA SCHEME II

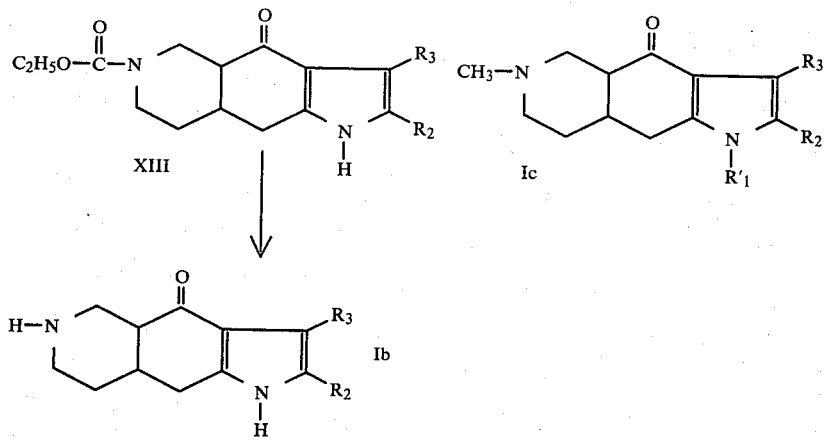

wherein $R_2$ and $R_3$ are as previously described, and $R_1'$ is alkyl, alkanoyl, aroyl or aralkyl.

In accordance with Formula Scheme II, compounds of formulas Ib and Ic are prepared by alkylation or acylation of the pyrrole nitrogen of a compound of formula Ia' and other N-6-alkyl derivatives by formation of the pyrrole anion with strong base, for example, sodium amide, potassium hydride, sodium methylsulfinylcarbanion, or butyllithium, or with an alkali metal followed by quenching with an alkyl or acyl halide in a solvent such as tetrahydrofuran, dioxane, ethyl ether, dimethylformamide or dimethylsulfoxide. For example, treatment of a compound of formula Ia', wherein $R_2$ is methyl and $R_3$ is ethyl, with sodium in liquid ammonia followed by quenching with methyl iodide affords the 1-methyl derivative, i.e., a compound of formula Ic wherein $R_2$ is methyl, $R_3$ is ethyl, and $R_1'$ is methyl. Similarly, reaction of a compound of formula Ia', wherein $R_2$ is methyl and $R_3$ is ethyl, with butyllithium in tetrahydrofuran at $-30°$ followed by quenching with benzoyl chloride affords the 1-benzoyl derivative, i.e., a compound of formula Ic wherein $R_1'$ is benzoyl, $R_2$ is methyl and $R_3$ is ethyl.

N-Demethylation of the compound of formula Ia' can be accomplished by standard N-dealkylation procedures, such as the von Braun method [H. A. Hageman, *Org. Reactions*, 7, 198 (1953)], or via acid or base hydrolysis of a urethane derivative such as those listed in K. C. Rice [J. Org. Chem., 40, 1850 (1975)]. One procedure for the dealkylation of the compound of formula Ia' was via the urethane of formula XIII and acid hydrolysis to give the secondary amine of formula Ib. For example, a compound of formula Ia', wherein $R_2$ is methyl and $R_3$ is ethyl was refluxed in diethyl ketone with excess ethyl chloroformate and potassium bicarbonate for 3 hours to give a compound of formula XIII, wherein $R_2$ is methyl and $R_3$ is ethyl. Hydrolysis of the foregoing compound with concentrated hydrochloric acid in acetic acid at reflux for 24 hours gave a compound of formula Ib, wherein $R_2$ is methyl and $R_3$ is ethyl. The same compound was obtained by hydrolysis of the urethane of formula XIII with sodium hydroxide in refluxing ethanol.

FORMULA SCHEME III

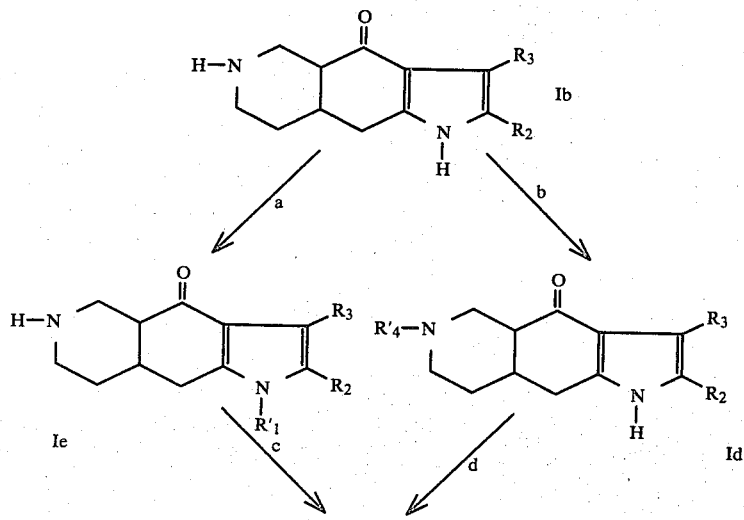

FORMULA SCHEME III

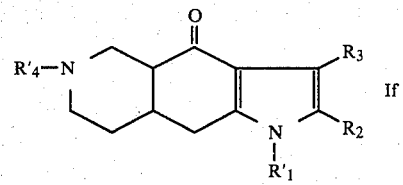

wherein $R_2$ and $R_3$ are as previously described, and $R_1'$ is alkyl, alkanoyl, aroyl or aralkyl, and $R_4'$ is alkyl, hydroxyalkyl, phenylhydroxyalkyl, halophenyl-hydroxyalkyl, alkylphenyl-hydroxyalkyl, alkoxyphenyl-hydroxyalkyl, alkoxyalkyl, aryloxy-hydroxyalkyl, alkoxy-hydroxyalkyl, acyloxyalkyl, arylcarbonylalkyl, alkoxycarbonylalkyl, aralkyl, alkenyl, alkyl-cycloalkyl, thienyl-alkyl, alkynyl, furyl-alkyl, arylcarboxamidoalkyl, acylalkyl, cyclic-alkyloxoalkyl, cyclic-alkylhydroxyalkyl, alkenyloxyalkyl, aralkenyl, aryloxyalkyl, N-alkyl-pyrrolidinylalkyl, trifluoroalkyl of 2 to 6 carbon atoms, aryl-N-imidazolonylalkyl, or

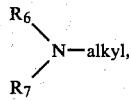

wherein $R_6$ and $R_7$, independently, are hydrogen or alkyl, or taken together with the nitrogen, are a 5- or 6-membered heterocyclic ring.

In accordance with Formula Scheme III, the compounds of formulas Id, Ie and If are prepared from the secondary amine of formula Ib, the starting material for the preparation of numerous derivatives encompassed by formula I, by substitution at the basic amine nitrogen (N-6) and/or the pyrrole nitrogen (N-1). For example, treatment of a compound of formula Ib with an alkyl halide, such as ethyl bromide, an alkenyl halide, such as allyl bromide, a cycloalkyl-halide, such as chloromethylcyclopropane, or an aralkyl halide, such as benzyl bromide, in the presence of a base, for example, potassium carbonate, in acetone, 2-propanone or dimethylformamide, yields the correspondingly substituted compound of formula Id, that is, wherein $R_4'$ is alkyl, alkenyl, cycloalkyl-alkyl or aralkyl, respectively. With reactive halides, the reaction may be run at room temperature; with less reactive halides, reflux temperatures are used, and in some cases, the reaction rate can be enhanced by the addition of an iodide salt, such as lithium iodide, to the reaction mixture.

Reaction of a compound of formula Ib with epoxyalkanes gives the hydroxyalkyl substituted compound of formula Id. Treatment with a substituted epoxyalkane gives the 2-substituted-2-hydroxyalkyl analogs of a compound of formula Id, for example, reaction of a compound of formula Ib with styrene oxide gives a compound of formula Id, wherein $R_4'$ is 2-phenyl-2-hydroxyethyl. The reaction is usually carried out in the presence of an alcoholic solvent such as methanol, at from about room temperature to the reflux temperature of the mixture. The epoxyalkanes are either commercially available or are prepared by epoxidation of the corresponding olefins, or by methylenation of a ketone with a sulfoniummethylide or sulfoxonium methylide reagent, for example, dimethylsulfonium methylide.

Thus, for example, treatment of benzaldehyde with dimethylsulfonium methylide gives styrene oxide.

The compound of formula Ib may be converted to the compound of formula Ie by a process in which, successively, the basic amine nitrogen (N-6) of the compound of formula Ib is protected with a hydrolyzable or hydrogenolyzable protecting group, substituted at the pyrrole nitrogen (N-1), and deprotected. Typical protecting groups are acetyl, t-butoxycarbonyl, benzenesulfonyl, or benzyl. The reaction of the protected intermediate is carried out substantially as described for the conversion of the compound of formula Ia to the compound of formula Ic. The substituted intermediate is deprotected by base or acid hydrolysis or hydrogenolysis methods appropriate to the protecting group. For example, the compound of formula Ib where $R_2$ is methyl and $R_3$ is ethyl, is treated with formic acetic anhydride to yield the 6-formyl derivative. Treatment of the derivative with sodium hydride in dimethylsulfoxide followed by treatment with methyl iodide and acid hydrolysis yields the compound of formula Ie where $R_1'$ is methyl, $R_2$ is methyl, and $R_3$ is ethyl.

Treatment of a compound of formula Ib with a haloalkylamine in the presence of a base, for example, potassium carbonate, or an aziridine yields amine-substituted analogs of a compound of formula Id, respectively. The reaction conditions are as described for the preparation of alkyl derivatives.

In some cases, where $R_4'$ in the compound of formula Id does not contain functional groups capable of undergoing alkylation or acylation, the procedures outlined in Formula Scheme III can be used directly to prepare N-1 substituted analogs of formula If. Alkylations can occur in compounds wherein $R_4'$ is hydroxyalkyl, phenylhydroxyalkyl, halophenyl-hydroxyalkyl, alkylphenyl-hydroxyalkyl, alkoxyphenol-hydroxyalkyl, aryloxy-hydroxyalkyl, alkoxy-hydroxyalkyl, cyclic-alkylhydroxyalkyl, or

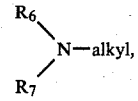

wherein $R_6$ and $R_7$, independently, are hydrogen or alkyl, or taken together with the nitrogen, are a 5- or 6-membered heterocyclic ring. The functional groups therein, for example, hydroxyl or secondary amino, must be protected with a base-stable protecting group, such as tetrahydropyranyl. After N-1 alkylation, the protecting group is removed by acid hydrolysis.

The compound of formula Ie is converted to the compound of formula If using substantially the same procedure used in the conversion of the compound of formula Ib to the compound of formula Id.

In the reactions described in Formula Schemes I, II and III, both the trans isomers of the formula:

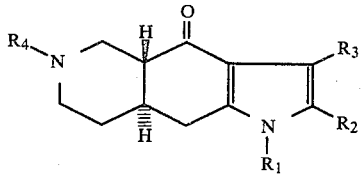

wherein $R_1$, $R_2$, $R_3$ and $R_4$ are as previously described, and cis isomers of the formula:

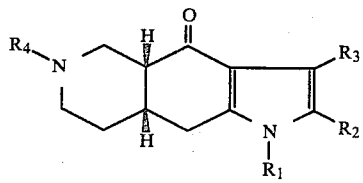

wherein $R_1$, $R_2$, $R_3$ and $R_4$ are as previously described, of the compounds of formula I may be formed, with the trans isomer predominating. The pure trans isomer may be separated by chromatography or crystallization. In addition, the mixture may be isomerized as described for the isomerization of the trans and cis isomers of the oxo compound of formula I′a and I″a.

pyrrole ring. In accordance with Formula Scheme IV, the (3,5-dimethoxyphenyl)-ethylamine of formula IV is refluxed with aqueous formaldehyde to give the tetrahydroisoquinoline of formula X. Birch reduction of the tetrahydroisoquinoline of formula X with lithium in liquid ammonia containing t-butanol under conditions substantially the same as described for the Birch reduction of the compound of formula IV yields the hexahydroisoquinoline of formula XI. Hydrolysis of crude hexahydroisoquinoline of formula XI under conditions substantially the same as described for the hydrolysis of the dihydroamine of the formula V yields the diketone of formula XII. The compound of formula XII is reacted in a Knorr condensation, as described in the preparation of the dihydroindolone-ethylamine of formula IX with the isonitrosoketone of formula VII or with the aminocarbonyl compound of formula VIII to give the pyrroloisoquinoline of formula Ia. Preferred is the sequence of reactions in accordance with Formula Scheme IV starting with the amine of formula IV, wherein $R_4''$ is methyl, giving the corresponding N-methyl-pyrroloisoquinoline of formula Ia, as a mixture containing the trans isomer I′a and the cis isomer of formula I″a.

The same procedures for isomerization of the mixture of pyrroloisoquinolines of formulas I′a and I″a as described previously may be employed to yield mainly the trans isomer of formula I′a.

The compounds of formula A wherein X is S are characterized by the formula:

FORMULA SCHEME IV

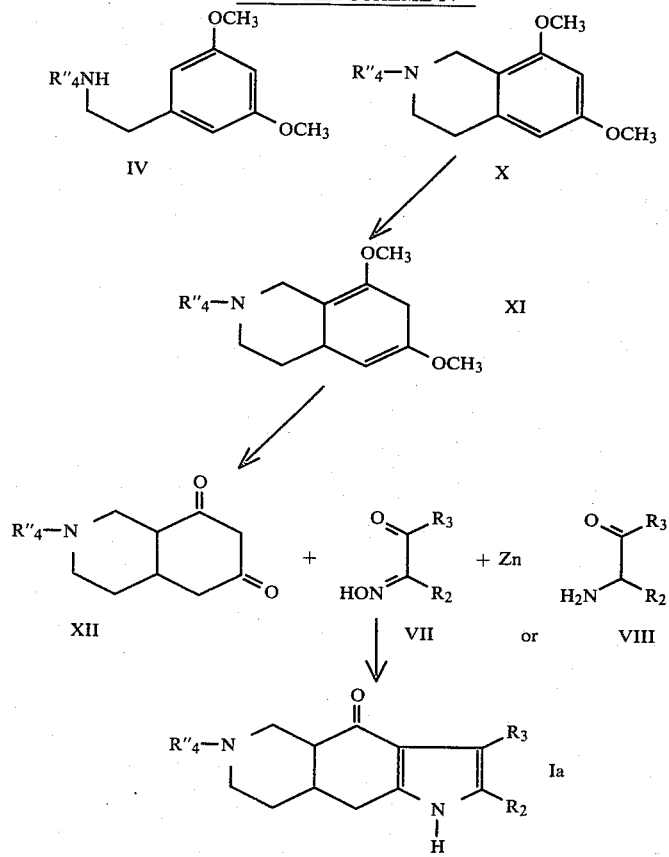

wherein $R_2$ and $R_3$ are as previously described, and $R_4''$ is alkyl, alkoxyalkyl, or alkyl-cycloalkyl.

An alternative synthesis of the compounds of formula Ia is described in Formula Scheme IV, in which the isoquinoline ring is formed prior to the formation of the

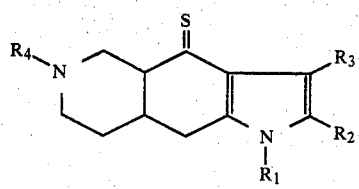

II wherein $R_1$, $R_2$, $R_3$ and $R_4$ are as hereinbefore described, and can be prepared as set forth hereinafter.

Thione compounds of formula II are generally prepared by reaction of phosphorus pentasulfide on keto compounds of formula I. When the compound of formula I has no functional groups capable of reacting with phosphorus pentasulfide besides the 4-oxo group, then the compound of formula I may be converted to the compound of formula II directly by heating with phosphorus pentasulfide in an inert organic solvent. On the other hand, when the compound of formula I does contain functional groups capable of reacting with phosphorus pentasulfide, for example, when $R_4$ is other than hydrogen, alkyl, alkoxyalkyl, aralkyl, alkenyl, alkyl-cycloalkyl, alkynyl, thienyl-alkyl, furyl-alkyl, alkenyloxyalkl, aralkenyl, aryloxyalkyl, or trifluoroalkyl of 2 to 6 carbon atoms, or when $R_2$ or $R_3$ is acyl, these groups must be protected before the reaction and deprotected thereafter. For example, keto groups may be protected as a ketal such as ethylene ketal and alcohol groups may be protected as an ether derivative, such as a benzyl ether. Alternatively, thiones of formula II may be made by suitable procedures described in Formula Schemes V and VI.

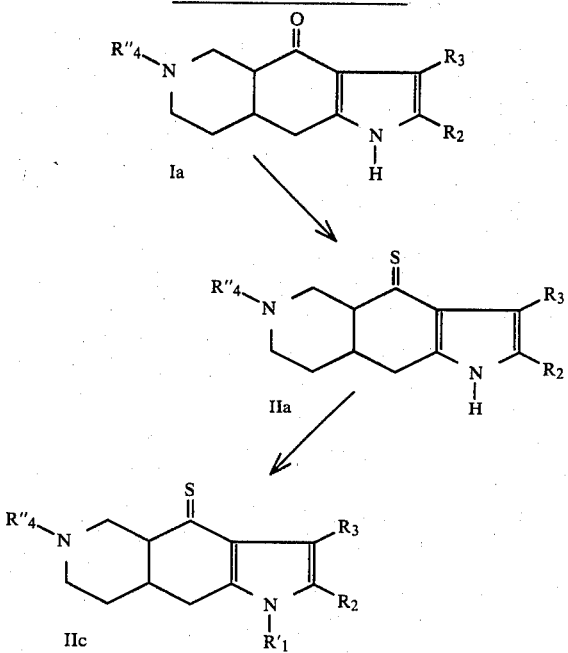

wherein $R_1'$, $R_2$, $R_3$ and $R_4''$ are as hereinbefore described.

In Formula Scheme V, the compound of formula Ia is converted to the compound of formula IIa by heating in an inert organic solvent with phosphorus pentasulfide. Preferred solvents are tetrahydrofuran, benzene, and dioxane, and the reaction is generally run at reflux temperature. The compound of formula IIa may then be alkylated or acylated to the compound of formula IIc in the same manner described in Formula Scheme II for the conversion of the compound of formula Ia' to the compound of formula Ic.

Additional compounds of formula II can be made as described in Formula Scheme VI:

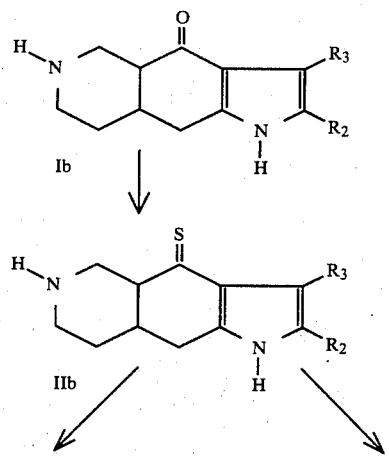

FORMULA SCHEME VI

-continued

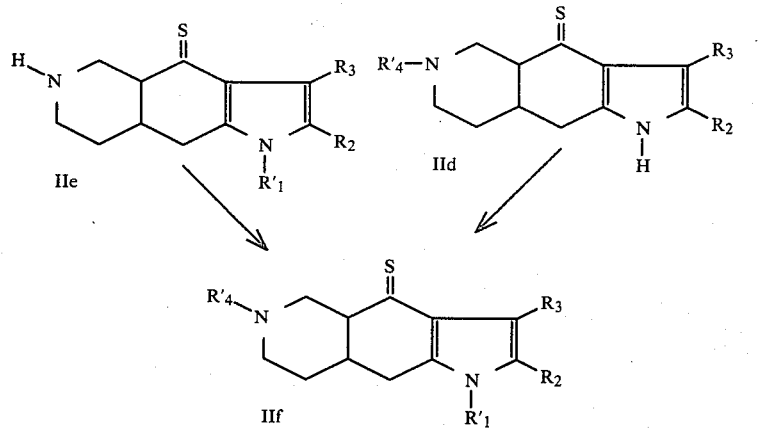

wherein $R_2$, $R_3$, $R_1'$ and $R_4'$ are as previously described.

In Formula Scheme VI, the compound of formula Ib is reacted with phosphorus pentasulfide as above described, to afford the thione of formula IIb. Subsequent transformations of the compound of formula IIb to the compounds of formulas IId, IIe and IIf are performed in the same manner as described in Formula Scheme III for the analogous oxo compound Ib in its conversions to the compounds of formulas Id, Ie and If.

In these reactions, both the trans isomers of the formula:

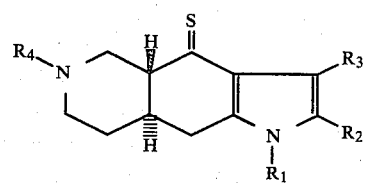  II' wherein $R_1$, $R_2$, $R_3$ and $R_4$ are as previously described, and cis isomers of the formula:

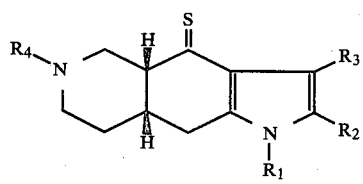  II'' wherein $R_1$, $R_2$, $R_3$ and $R_4$ are as previously described, of the compounds of formula II may be formed, with the trans isomer predominating. The pure trans isomer may be separated by chromatography or crystallization. In addition, the mixture may be isomerized as described for the isomerization of the trans and cis isomers of the oxo compound of formula I'a and I''a.

The compounds of formula A form acid addition salts with inorganic or organic acids. Thus, they form pharmaceutically acceptable acid addition salts with both pharmaceutically acceptable organic and inorganic acids, for example, with hydrohalic acid, such as, hydrochloric acid, hydrobromic acid, hydroiodic acid, other mineral acid salts, such as sulfuric acid, nitric acid, phosphoric acid, or the like, alkyl- and mono-aryl sulfonic acids, such as ethanesulfonic acid, toluenesulfonic acid, benzenesulfonic acid, or the like, other organic acids such as acetic acid, tartaric acid, maleic acid, citric acid, benzoic acid, salicylic acid, ascorbic acid, and the like. Non-pharmaceutically acceptable acid addition salts of compounds of formula A can be converted into pharmaceutically acceptable acid addition salts via conventional metathetic reactions whereby the non-pharmaceutically acceptable anion is replaced by a pharmaceutically acceptable anion; or alternatively; by neutralizing the non-pharmaceutically acceptable acid addition salt and then reacting the so-obtained free base with a reagent yielding a pharmaceutically acceptable acid addition salt. The acid addition salts may also form hydrates.

The compounds of formula A and their pharmaceutically acceptable acid addition salts exhibit neuroleptic activity. Significantly, however, they lack hypotensive activity, and demonstrate only weak cataleptic activity. Accordingly, the compounds of formula A are useful as antipsychotic agents, for instance, in the treatment of schizophrenia. The activity of the compounds of formula A which makes them useful as antipsychotic agents can be demonstrated in warm-blooded animals, in accordance with known procedures.

For example, by one procedure, trained rats are placed in experimental chambers equipped with a response lever, a steel grid floor for delivery of electric shock and a loudspeaker for presentation of auditory stimuli. Each trial consists of a fifteen-second warning tone, (conditioned stimulus), continuing for an additional fifteen seconds accompanied by electric shock (unconditioned stimulus; 1.0 mA, 350 V.A.C.). The rats can terminate a trial at any point by depression of the response lever. A response during the initial fifteen-second warning tone ends the trial before shock delivery and is considered an avoidance response, while a response occurring during shock delivery is an escape response. Trials are presented every two minutes during a one-hour test session (30 trials per session).

Trained rats maintain a reliable control baseline of avoidance behavior (zero to three avoidance failures per session). Compounds are administered at appropriate pretreatment times to a minimum of three to four rats at each dose level over a range of doses. Rats receive vehicle alone, during control sessions. One control and one experimental session are alternated during each week; each animal serves as his own control.

The session is divided into three consecutive twenty minute (ten trial) segments. Response counts are summed over all subjects at a given dose within each segment.

The number of trials in which the rats failed to exhibit an avoidance response (avoidance block; AB) or failed to exhibit an escape response (escape block; EB) is determined for the segment displaying the maximum such effect at each dose. This number is expressed as a percentage of the total trials within the segment. The dose calculated to produce a 50% block of avoidance (AB 50) is obtained from the dose-effect regression line fitted by the Method of Least Squares. The lowest dose which produced a 20% block of escape responding (EB 20) is read from a graphic dose-effect plot. In obtaining these values, percent effect is plotted against the log dose.

Antipsychotic agents can be distinguished from other types of drugs, which affect the behavior of rats in this procedure, by the larger separation between doses which block avoidance responding and doses which block escape responding. The clinical potency of antipsychotic drugs with known therapeutic uses and properties is significantly and highly correlated with their potency in this procedure. Consequently, the compounds of formula A may be used therapeutically in dosage ranges consistent with their potency in the text procedure.

When 3-ethyl-2,6-dimethyl-4,4a,5,6,7,8,8a,9-octahydro-4a,8a-trans-1H-pyrrolo-[2,3-g]isoquinolin-4-one, hydrochloride, which has demonstrated an $LD_{50}$ of, for example, 350 mg/kg p.o. in mice, is utilized as the test substance, neuroleptic activity is observed at an $AB_{50}$ of 0.7 mg/kg p.o. and 0.095 mg/kg s.c. In the (-)-enantiomer of the foregoing compound, neuroleptic activity is observed at an $AB_{50}$ of 0.48 mg/kg p.o.

Similarly, when 2,3,6-trimethyl-4,4a,5,6,7,8,8a,9-octahydro-4a,8a-trans-1H-pyrolo[2,3-g]isoquinolin-4-one, hydrochloride is utilized as the test substance, neuroleptic activity is observed at an $AB_{50}$ of 0.48 mg/kg p.o.

Similarly, when N-[2(3-ethyl-4,4a,5,6,7,8,8a,9-octahydro-2-methyl-4-oxo-4a,8a-trans-1H-pyrrolo[2,3-g]isoquinolin-6-yl)ethyl]-4-fluorobenzamide is utilized as the test substance, neuroleptic activity is observed at an $AB_{50}$ of 3.5 mg/kg p.o.

Similarly, when 3-ethyl-2-methyl-6-[4-(4-fluorophenyl)-4-oxobutyl]-4,4a,5,6,7,8,8a,9-octahydro-4a,8a-trans-1H-pyrrolo[2,3-g]isoquinolin-4-one is utilized as the test substance, neuroleptic activity is observed at an $AB_{50}$ of 0.19 mg/kg p.o.

Similarly, when 3-ethyl-2,6-dimethyl-4,4a,5,6,7,8,8a,9-octahydro-4a,8a-trans-1H-pyrrolo[2,3-g]isoquinolin-4-thione is utilized as the test substance, neuroleptic activity is observed at an $AB_{50}$ of 0.94 mg/kg p.o.

The compounds of formula A and their pharmaceutically acceptable acid addition salts have antipsychotic effects which are qualitatively similar to those of haloperidol, trifluoroperazine and molindone, known for their therapeutic uses and properties. Thus, the compounds of formula A demonstrate a pattern of activity associated with antipsychotic drugs of known efficacy and safety.

The compounds of formula A and their pharmaceutically acceptable acid addition salts can be used in the form of conventional pharmaceutical preparations. By way of exemplification, suitable oral dosage units comprise or are in the range of from 0.05 to 50 mg., and suitable oral dosage regimens in warm-blooded animals comprise or are in the range of from about 0.001 mg/kg per day to about 10 mg/kg per day. However, for any particular warm-blooded animal, the specific dosage regimen may be variable and should be adjusted according to individual need and the professional judgment of the person administering or supervising the administration of a compound of formula A or a pharmaceutically acceptable acid addition salt thereof. Furthermore, the frequency with which any such dosage form will be administered will vary, depending upon the quantity of active medicament present therein and the needs and requirements of the pharmacological situation.

For the disclosed use, the compounds of formula A and their pharmaceutically acceptable acid addition salts are formulated, using conventional inert pharmaceutical adjuvant materials, into dosage forms which are suitable for oral or parenteral administration. Such dosage forms include tablets, suspensions, solutions, and the like. Furthermore, the compounds of formula A can be embodied into, and administered in the form of, suitable hard or soft capsules. The identity of the inert adjuvant materials which are used in formulating the compounds of formula A and their pharmaceutically acceptable acid addition salts into oral and parenteral dosage forms will be immediately apparent to persons skilled in the art. These adjuvant materials, either inorganic or organic in nature, include, for example, water, gelatin, lactose, starch, magnesium stearate, talc, vegetable oils, gums, polyalkylene glycols, etc. Moreover, preservatives, stabilizers, wetting agents, emulsifying agents, salts for altering osmotic pressure, buffers, or the like, can be incorporated, if desired, into such formulations.

Since the compounds of formula A and their pharmaceutically acceptable acid addition salts possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active resolving agent, for example, an optically active acid, such as (+)-tartaric acid to form a diastereomeric salt. The formed diastereomers are separated by fractional crystallization and can be converted to the corresponding optical isomer base. Thus, the invention covers the optically active isomers of the compounds of formula A as well as their racemates.

Furthermore, due to the possible different spatial arrangements of their atoms, it is to be understood that the compounds of this invention may be obtained in more than one possible geometric isomeric form. The compounds of formula A, as described and claimed, are intended to embrace all such isomeric forms. Accordingly, the examples included herein are to be understood as illustrative of particular mixtures of geometric isomers or single geometric isomers and not as limitations upon the scope of the invention.

The Examples which follow further illustrate the invention. All temperatures are in degrees Centigrade, unless otherwise stated.

EXAMPLE 1

Preparation of N-2-(3,5-dimethoxyphenyl)-ethyl carbamic acid, ethyl ester

In a 5 l. 3-neck round-bottom flask fitted with a mechanical stirrer and addition funnel were placed 32.63 g. of (3,5-dimethoxyphenyl)-ethylamine hydrochloride, 600 ml. of water, 600 ml. of dichloromethane and 150 ml. of 1N sodium hydroxide solution. The mixture was stirred and cooled in an ice bath while 16.28 g. of ethyl chloroformate in 60 ml. of dichloromethane was added dropwise over 30 min. During the addition, a total of 150 ml. of 1N sodium hydroxide solution was added in 8 portions to keep the pH between 8 and 9. After the addition was complete, the mixture was stirred in the ice bath for 1 hour. The mixture was transferred to a separatory funnel and the organic layer was separated. The aqueous solution was extracted with 200 ml. of dichloromethane and the organic solutions were combined and washed with 100 ml. of water and 100 ml. of brine and dried over anhydrous sodium sulfate and filtered. The filtrate was concentrated on a rotary evaporator to give 37.1 g. of crude N-2-(3,5-dimethoxyphenyl)-ethyl carbamic acid, ethyl ester as a colorless oil.

EXAMPLE 1a

Preparation of N-methyl-(3,5-dimethoxyphenyl)-ethylamine hydrochloride

In a 3 l. 3-neck round-bottom flask equipped with a mechanical stirrer, addition funnel, and condenser were placed 180 ml. of 70% sodium dihydrobis(2-methoxyethoxy)aluminate solution and 700 ml. of dry tetrahydrofuran. The solution was cooled in an ice bath and a solution of 37.1 g. of crude N-2-(3,5-dimethoxyphenyl)-ethyl carbamic acid, ethyl ester in 100 ml. of dry tetrahydrofuran was added over 15 minutes. After the addition, the mixture was heated to reflux for 1 hour and then was cooled in an ice bath. Excess hydride was decomposed by the dropwise addition of 100 ml. of 5% sodium hydroxide solution. After all the base had been added, the organic layer was separated and the aqueous extracted with 100 ml. of ether. The combined organic solutions were concentrated to an oil on a rotary evaporator and the oil was dissolved in 300 ml. of ether. The ether solution was washed with 50 ml. of water, 50 ml. of brine, dried over anhydrous sodium sulfate, and filtered. To the filtrate was added 70 ml. of ethereal hydrogen chloride to precipitate the amine hydrochloride. The solid was collected on a Buchner funnel and was crystallized from 180 ml. of absolute ethanol and 270 ml. of ether to give 28.9 g. of N-methyl-(3,5-dimethoxyphenyl)-ethylamine hydrochloride as a white, crystalline solid, mp 160°–164°.

EXAMPLE 2

Preparation of N-methyl-1,5-dimethoxycyclohexa-1,4-diene-3-ethylamine 185.2 g. of N-methyl-(3,5-dimethoxyphenyl)-ethylamine hydrochloride was dissolved in 1600 ml. of water and the solution was made alkaline with 160 ml. of ammonium hydroxide. The mixture was extracted with 3×1000 ml. of dichloromethane and the combined extracts were washed with 1000 ml. of brine and dried over anhydrous sodium sulfate. Evaporation of the solvent on a rotary evaporator at 35°–40° gave 156.0 g. of free base.

In a 12 l. 3-neck flask equipped with a mechanical stirrer and two dry ice condensers, one fitted with a gas inlet and the other with a soda-lime drying tube was condensed 4.0 l. of anhydrous ammonia. To the ammonia was added a solution of 156.0 g. of the free base in 400 ml. of t-butanol and 400 ml. of anhydrous ether over 15 minutes. To the stirred solution was added over 50 min. a total of 33.6 g. of lithium wire cut into 2.5 in. lengths. The addition rate was controlled so that 5 in. of wire was added per minute. After all the lithium had been added, the deep blue mixture was stirred under reflux for 2 hours. Then 2.8 l. of anhydrous ether was added to dilute the mixture, the drying tube was removed to allow the hydrogen to vent, and a total of 280 g. of ammonium chloride powder was added slowly over 30 minutes until the blue color had dissipated. The dry ice condenser was removed and the mixture was stirred and the ammonia allowed to evaporate overnight. To the residue was added 2.8 l. of ice water. The mixture was transferred to a separatory funnel, rinsing with 800 ml. of ether, and the layers were separated. The aqueous layer was extracted with 2×1.5 l. of dichloromethane and the extracts were combined and washed with 1 l. of brine and dried over anhydrous sodium sulfate. Evaporation of the solvents on a rotary evaporator at 40° and finally at 40°/1.0 mm. for 1.5 hours afforded 150.7 g. of crude product as a yellow oil. The crude oil was distilled through a 12-in. Goodloe column (bath 150°) collecting fractions as follows:

| Fraction | bp | wt | gc purity |
|---|---|---|---|
| 1 | 40–80°/0.45 mm. | 7.9 g. | 4.6% |
| 2 | 80–85°/0.45 to 0.15 mm. | 6.2 g. | 50% |
| 3 | 85–86°/0.15 mm. | 21.2 g. | 92% |
| 4 | 86–87°/0.15 mm. | 99.4 g. | 100% |

Fractions 3 and 4 combined afforded 120.6 g. of N-methyl-1,5-dimethoxycyclohexa-1,4-diene-3-ethylamine as a colorless oil.

EXAMPLE 3

Preparation of 6-[2-(N-methylamino)ethyl]-2-methyl-3-ethyl-6,7-dihydro-(5H)-4(1H,5H)indolone In a 1 l. 3-neck round-bottom flask equipped with a mechanical stirrer and condenser was placed a solution of 60.0 g. of distilled N-methyl-1,5-dimethoxycyclohexa-1,4-diene-3-ethylamine in 700 ml. of 70% aqueous acetic acid. The reaction mixture was refluxed for 15 minutes and 59.5 g. of zinc dust was added in five portions over 10 minutes and then the mixture was refluxed for another 15 minutes. To the refluxing solution was added a solution of 42.1 g. of 2-isonitroso-3-pentanone in 175 ml. of 70% aqueous acetic acid over a period of 1 hour. After the addition, the mixture was refluxed for 2.5 hours and cooled to room temperature. The precipitated zinc acetate was removed by filtration and the filter cake was washed with 500 ml. of dichloromethane. The filtrate was concentrated on a rotary evaporator and the residue heated at 100°/1.0 mm. for 30 minutes to remove last traces of acetic acid. The residue was dissolved in 500 ml. of water and the solution was extracted with 2×150 ml. of dichloromethane. The dichloromethane extracts were discarded and the aqueous layer was made basic (pH 8-9) with 165 ml. of ammonium hydroxide and 500 ml. of brine was added. The mixture was extracted with 3×200 ml. of dichloromethane and the combined extract was washed with 100 ml. of brine and was dried over anhydrous sodium sulfate. Evaporation of the solvent afforded 56.0 g. of crude tetrahydroindolone which was dissolved in 90 ml. of 2:1 toluene-ethyl acetate. The solution was stirred magnetically and was seeded and allowed to crystallize overnight with stirring. The first crop of 20.8 g. was collected by filtration and the mother liquor was concentrated and crystallized again from a stirred solution to give 10.0 g. in the second crop. The mother liquor was dissolved in 75 ml. of methanol and a solution of 15.0 g. of oxalic acid in 50 ml. of methanol was added. The mixture was warmed 10 minutes on the steam bath and cooled. The solid oxalate salt was filtered off and washed with 10 ml. of methanol and dissolved in 50 ml. of water. The solution was made basic with ammonium hydroxide and extracted with 2×50 ml. of dichloromethane. The extracts were washed with 1×20 ml. of brine and dried over anhydrous sodium sulfate and concentrated on a rotary evaporator to give 4.5 g. of additional crude product. Crystallization from 2:1 toluene-ethyl acetate afforded 2.6 g. of additional crystalline product. The two crops and oxalate-derived crystals were combined and dried at 25°/1 mm. for 2 hours to give 33.4 g. of 6-[2-(N-methylamino)ethyl]-2-methyl-3-ethyl-6,7-dihydro-(5H)-4(1H,5H)-indolone as a light yellow solid, mp 114°-120°, which was homogenous by TLC.

EXAMPLE 4

Preparation of
3-ethyl-2,6-dimethyl-4,4a,5,6,7,8,8a,9-octahydro-4a,8a-trans-1H-pyrrolo[2,3-g]-isoquinolin-4-one, hydrochloride In a 500 ml. round-bottom flask was placed 17.0 g. of 6-[2-(N-methylamino)ethyl]-2-methyl-3-ethyl-6,7-dihydro-(5H)-4(1H,5H)-indolone and 170 ml. of methanol. To the solution was added 20 ml. of 4 N hydrogen chloride in diethyl ether (made by bubbling HCl gas into diethyl ether in an ice bath and titrating). The solvent was removed on a rotary evaporator and the residual solid was dried at 50°/1 mm for 2 hours to give 19.7 g. of crude hydrochloride salt.

In a 3-l. 3-neck round-bottom flask equipped with a mechanical stirrer, thermometer and distilling head were placed the 19.7 g. of hydrochloride salt, 21.8 g. of paraformaldehyde and 1000 ml. of octanol. The reaction mixture was heated to reflux and water which was liberated was removed by distillation until the temperature of the octanol solution in the flask reached 175°-180°, whereupon the distilling head was removed and replaced by a reflux condenser. The reaction mixture was heated at 175°-180° for 1 hour and 6.54 g. of paraformaldehyde was added in three portions over 5 minutes. Water was distilled out as before until the temperature reached 175°-180° and the mixture was heated at 175°-180° for an additional 1 hour. The dark brown solution was cooled and poured into 1000 ml. of water. The layers were separated and the organic layer was extracted with 2×400 ml. of 5% hydrochloric acid. The combined aqueous extract was washed with 2×150 ml. of chloroform and the chloroform solutions were discarded. To the aqueous layer were added 120 ml. of ammonium hydroxide and 400 ml. of chloroform. The layers were separated and the aqueous solution was extracted with 4×200 ml. of chloroform. The combined chloroform extracts were washed with 200 ml. of brine and dried over anhydrous sodium sulfate. Evaporation of the solvent afforded 12.0 g. of crude pyrrolo[2,3-g]isoquinoline as a 4a,8a-trans, 4a,8a-cis mixture (about 8:1) as a dark tan solid. The crude solid was dissolved in 100 ml. of 9:1 dichloromethane-methanol and 300 ml. of diethyl ether was added. The fine solid precipitate, predominantly the 4a,8a-trans isomer, was collected by filtration and the filtrate was concentrated and crystallized to give second and third crops of tan solid. The combined material was dried at 25°/1 mm. for 1 hour to give 8.20 g. of a light grey solid, 3-ethyl-2,6-dimethyl-4,4a,5,6,7,8,8a,9-octahydro-4a,8a-trans-1H-pyrrolo[2,3-g]-isoquinolin-4-one, mp 203°-226°. The partially-purified grey solid was suspended in 80 ml. of methanol and 12 ml. of 4 N hydrogen chloride in diethyl ether was added. The solvent was removed and the residue was crystallized from 25 ml. of hot absolute ethanol. The first crop was collected by filtration and the mother liquid was concentrated and crystallized to give second and third crops of crystals. The combined solid was dissolved in 120 ml. of methanol and 2.4 g. of activated carbon (Darco-G-60) was added. The mixture was warmed on a steam bath for 10 minutes and the carbon filtered off through celite. The filtrate was concentrated and recrystallized from 15 ml. of ethanol to give three crops of white crystals. The combined solid was dried under vacuum at 80°/0.05 mm. for 18 hours to give 5.4 g. of 3-ethyl-2,6-dimethyl-4,4a,5,6,7,8,8a,9-octahydro-4a,8a-trans-1H-pyrrolo[2,3-g]isoquinolin-4-one, hydrochloride as a white solid, mp 196°-198°; Oxime, semihydrate, mp 131°-133° C.

EXAMPLES 4a-c

Following the procedures of Examples 3 and 4, the compounds listed in Table I were prepared from the appropriate isonitrosoketone with variations as noted. Each compound displayed spectral characteristics which were consistent with the described structure. Melting points are for the free base or hydrochloride salt (.HCl) as indicated. Isonitrosoketones were prepared as described in the literature [e.g., Ferris et al., J. Org. Chem., 24, 1726 (1959)] by nitrosation of the appropriate ketone. The isolated compounds are the 4a,8a-trans isomers.

TABLE I

| Example | $R_2$ | $R_3$ | Analysis Calcd. | Found | mp | Crystallized from | Variation in procedure |
|---|---|---|---|---|---|---|---|
| 4a<br>3,6-dimethyl-2-(2-propyl)-4,4a,5,<br>6,7,8,8a,9-octahydro-1H-pyrrolo-<br>[2,3-g]isoquinolin-4-one | $CH(CH_3)_2$ | $CH_3$ | (.HCl)<br>C 64.74<br>H 8.49<br>N 9.44<br>Cl⁻ 11.94 | C 64.53<br>H 8.38<br>N 9.36<br>Cl⁻ 12.16 | (.HCl)<br>>280°,d | methanol | — |
| 4b<br>2,6-dimethyl-3-phenyl-4,4a,5,6,7,<br>8,8a,9-octahydro-1H-pyrrolo[2,3-g]-<br>isoquinolin-4-one | $CH_3$ | phenyl | C 77.23<br>H 7.53<br>N 9.52 | C 77.23<br>H 7.50<br>N 9.54 | >240°,d | ethanol-ethyl acetate | Mannich reaction in diethylene glycol monoethyl ether, 155°, 1 hour |
| 4c<br>2,3,6-trimethyl-4,4a,5,6,7,8,8a,9-<br>octahydro-1H-pyrrolo[2,3-g]iso-<br>quinolin-4-one | $CH_3$ | $CH_3$ | (.HCl)<br>C 62.56<br>H 7.88<br>N 10.42<br>Cl⁻ 13.19 | C 62.19<br>H 7.97<br>N 10.20<br>Cl⁻ 13.41 | 275–80°,d | ethanol-ether | Knorr reaction in n-butanol at 170°/50 psi |

EXAMPLE 5

Preparation of
2-methyl-3-ethyl-4,4a,5,6,7,8,8a,9-octahydro-4a,8a-trans-1H-pyrrolo[2,3-g]isoquinolin-4-one A mixture of 3-ethyl-2,6-dimethyl-4,4a,5,6,7,8,8a,9-octahydro-1H-pyrrolo[2,3-g]isoquinolin-4-one prepared as in Example 4 (4.92 g., 20 mmol), ethyl chloroformate (19.55 g., 180 mmol), and potassium bicarbonate (6.0 g., 60 mmol) in diethyl ketone (100 ml.) was heated to reflux for 3 hours. The mixture was cooled, filtered, and the filtrate concentrated on a rotary evaporator to dryness and the residue was dissolved in chloroform. The chloroform solution was washed with 5% aqueous hydrochloric acid, brine, and was dried over anhydrous sodium sulfate. Evaporation of the solvent afforded 4.90 g. of crude carbamate which was purified by chromatography on alumina III to give 3.70 g. of pure 6-ethoxycarbonyl-3-ethyl-2-methyl-4,4a,5,6,7,8-,8a,9-octahydro-1H-pyrrolo[2,3-g]isoquinolin-4-one.

The carbamate (3.7 g., 12.2 mmol), glacial acetic acid (45 ml.) and concentrated hydrochloric acid (60 ml.) were heated to reflux for 24 hours, cooled, and concentrated on a rotary evaporator. The residue was dissolved in water and extracted with chloroform (discarded) and the aqueous layer was made alkaline with ammonium hydroxide and was extracted with chloroform. The combined extracts were washed with brine and dried over anhydrous sodium sulfate and concentrated to give 2.72 g. of crude secondary amine. Treatment of the crude amine in ethanol with ethanolic hydrogen chloride gave the hydrochloride salt, which was crystallized from hot ethanol to afford 2.18 g. (47% yield) of 2-methyl-3-ethyl-4,4a,5,6,7,8,8a,9-octahydro-4a,8a-trans-1H-pyrrolo[2,3-g]isoquinolin-4-one, hydrochloride as white crystals, mp>250°.

Anal. Calcd. for $C_{14}H_{20}N_2O \cdot HCl$: C, 62.56; H, 7.88; N, 10.42; Cl⁻, 12.19; Found: C, 62.50; H, 7.90; N, 10.19; Cl⁻, 13.33.

In an analogous manner, 2,3-dimethyl-4,4a,5,6,7,8-,8a,9-octahydro-4a,8a-trans-1H-pyrrolo[2,3-g]isoquinolin-4-one can be prepared from 2,3,6-trimethyl-4,4a,5,6,7,8,8a,9-octahydro-1H-pyrrolo[2,3-g]isoquinolin-4-one.

EXAMPLE 6

Preparation of
3,4-Dihydro-1H-6,8-dimethoxy-2-methyl-isoquinoline, hydrochloride A solution of N-methyl-(3,5-dimethoxyphenyl)ethylamine hydrochloride (15.0 g, 64.7 mmol) in 30 ml. of water was treated with 35 ml. of 2 N sodium hydroxide and extracted with dichloromethane. The combined extracts were concentrated on a rotary evaporator and mixed with aqueous formaldehyde (65 ml, 37% solution). The mixture was refluxed for 2 hours, made alkaline with 2 N sodium hydroxide (15 ml.) and extracted with dichloromethane. The combined extracts were washed with brine and dried over anhydrous magnesium sulfate and concentrated to give the product as a yellow oil (15.5 g). The oil was dissolved in 100 ml. of ethanol and treated with ethanolic hydrogen chloride. Ether (75 ml.) was added, and the salt crystallized to give 10.15 g. of 3,4-dihydro-1H-6,8-dimethoxy-2-methylisoquinoline, hydrochloride (64% yield).

EXAMPLE 7

Preparation of
1,2,3,4,4a,7-hexahydro-6,8-dimethoxy-2-methylisoquinoline and octahydro-2-methylisoquinolin-6,8-dione Ammonia (150 ml) was condensed in a flask containing t-butanol (9.1 g, 123 mmol) and diethyl ether (50 ml). To the solution was added 3,4-dihydro-1H-6,8-dimethoxy-2-methylisoquinoline hydrochloride (1.0 g, 4.1 mmol). After stirring 2-3 minutes, lithium wire (0.57 g, 82 mmol) was added in short pieces over 30 minutes. The blue solution was stirred under reflux for 2.5 hours and solid ammonia chloride (4.5 g) was added until the blue color dissipated. Ether (100 ml) was added and the ammonia was allowed to evaporate overnight. Ice water (100 ml) was added and the organic phase was separated. The aqueous layer was extracted with ethyl acetate and chloroform. The combined extracts were washed with brine and dried over anhydrous magnesium sulfate and concentrated to give 1,2,3,4,4a,7-hexahydro-6,8-dimethoxy-2-methylisoquinoline (0.58 g, 68% yield) as a yellow oil.

The crude product (1.05 g) in 20 ml. of 70% aqueous acetic acid was refluxed for 5 hours and the acetic acid was removed on a rotary evaporator. The residue was dissolved in water and washed with chloroform. The aqueous phase was concentrated to a 10 ml. volume and chromatographed on Dowex AG 50WX 8 eluting with 2 molar aqueous pyridine to afford 0.11 g. of octahydro-2-methylisoquinolin-6,8-dione (11.6% yield) as a light yellow solid. Treatment with hydrochloric acid in methanol afforded the hydrochloride, mp 193°–196°.

EXAMPLE 8

Preparation of
3-ethyl-2,6-dimethyl-4,4a,5,6,7,8,8a,9-octahydro-1H-pyrrolo[2,3-g]isoquinolin-4-one via octahydro-2-methylisoquinolin-6,8-dione 1,2,3,4,4a,7-Hexahydro-6,8-dimethoxy-2-methylisoquinoline (0.56 g, 2.68 mmol) was heated to 90°–100° in 70% aqueous acetic acid (10 ml) to hydrolyze the bis(enolether) to the octahydro-2-methylisoquinolin-6,8-dione. To the hot solution was added zinc dust (0.6 g, 9.25 mmol) and 2-isonitroso-3-pentanone (0.7 g, 6.1 mmol). The mixture was refluxed for 3 hours, cooled and filtered to remove zinc and zinc acetate. The filtrate was concentrated to dryness on a rotary evaporator and the residue was dissolved in dichloromethane. To the solution was added ammonium hydroxide and the layers were separated. The organic layer was washed with brine and dried over anhydrous sodium sulfate and concentrated to give the crude product. Chromatography of the crude product on Alumina III afforded 3-ethyl-2,6-dimethyl-4,4a,5,6,7,8,8a,9-octahydro-1H-pyrrolo[2,3-g]isoquinolin-4-one as a white solid (0.19 g, 29% yield).

EXAMPLE 9

Preparation of
2,6-dimethyl-3-isopropyl-4,4a,5,6,7,8,8a,9-octahydro-4a,8a-trans-1H-pyrrolo[2,3-g]isoquinolin-4-one A solution of crude octahydro-2-methyl-isoquinolin-6,8-dione (approximately 12.5 mmol) and 2.4 g. (18 mmol) of 2-isonitroso-4-methyl-3-pentanone in 40 ml. of 70% aqueous acetic acid was treated with 2.6 g. (40 mmol) of zinc dust and slowly heated to reflux. After 1 hour the mixture was cooled slightly and an additional 0.4 g. of isonitrosoketone and 1.0 g. of zinc were added and the mixture stirred for 1.5 hours at reflux. The mixture was then cooled and filtered, and the filtrate concentrated at 50°/20 mmHg to give a yellow oil which was diluted with 50 ml. of water and made alkaline (pH 8-9) with ammonium hydroxide. The mixture was extracted with chloroform and the extracts were washed with brine and dried over sodium sulfate and concentrated to give 2.6 of crude product. The material was chromatographed (dry column) on 100 g. of silica gel eluting with the organic phase of a mixture prepared by equilibrating (by volume) 90 parts chloroform, 30 parts methanol, 10 parts water, and 6 parts acetic acid. The eluate fractions containing the product were evaporated, diluted with water, made alkaline (pH 8-9) with ammonium hydroxide, and extracted with chloroform. The extracts were dried over sodium sulfate and evaporated to give 1.0 g. of solid product which was recrystallized twice from ethyl acetate to give 470 mg. of pure 2,6-dimethyl-3-isopropyl-4,4a,5,6,7,8,8a,9-octahydro-4a,8a-trans-1H-pyrrolo[2,3-g]isoquinolin-4-one as a crystalline solid, mp 244°–247° C.

EXAMPLE 10

Preparation of
3,6-dimethyl-2-(2-propenyl)-4,4a,5,6,7,8,8a,9-octahydro-4a,8a-trans-1H-pyrrolo[2,3-g]isoquinolin-4-one In a similar manner to that described in Example 9, 3-isonitroso-5-hexen-2-one and 2-methyl-octahydroisoquinolin-6,8-dione afforded 3,6-dimethyl-2-(2-propenyl)-4,4a,5,6,7,8,8a,9-octahydro-4a,8a-trans-1H-pyrrolo[2,3-g]isoquinolin-4-one, mp 221°–223° C.

EXAMPLE 11

Preparation of
3-cyclopropyl-2,6-dimethyl-4,4a,5,6,7,8,8a,9-octahydro-4a,8a-trans-1H-pyrrolo[2,3-g]isoquinolin-4one In a similar manner to that described in Example 9, cyclopropyl-2-isonitroso-1-propanone and 2-methyl-octahydroisoquinolin-6,8-dione afforded 3-cyclopropyl-2,6-dimethyl-4,4a,5,6,7,8,8a,9-octahydro-4a,8a-trans-1H-pyrrolo[2,3-g]isoquinolin-4-one, mp 258°–259° C. (dec.).

EXAMPLE 12

Preparation of
2-benzyl-3,6-dimethyl-4,4a,5,6,7,8,8a,9-octahydro-4a,8a-trans-1H-pyrrolo[2,3-g]isoquinolin-4-one In a similar manner to that described in Example 9, 3-isonitroso-4-phenyl-2-butanone and 2-methyl-octahydroisoquinolin-6,8-dione afforded 2-benzyl-3,6-dimethyl-4,4a,5,6,7,8,8a,9-octahydro-4a,8a-trans-1H-pyrrolo[2,3-g]isoquinolin-4-one, mp 234°–235° C.

EXAMPLE 13

Preparation of
6-methyl-4,4a,5,6,7,8,8a,9-octahydro-4a,8a-trans-1H-pyrrolo[2,3-g]isoquinolin-4-one In a similar manner to that described in Example 9, except that no zinc was used, aminoacetaldehyde dimethyl acetal and 2-methyl-octahydroisoquinolin-6,8-dione afforded 6-methyl-4,4a,5,6,7,8,8a,9-octahydro-4a,8a-trans-1H-pyrrolo[2,3-g]isoquinolin-4-one, mp 208°–210° C.

EXAMPLE 14

Preparation of
3-ethyl-1,2,6-trimethyl-4,4a,5,6,7,8,8a,9-octahydro-4a,-8a-trans-1H-pyrrolo[2,3-g]isoquinolin-4-one Liquid ammonia (80 ml) was condensed into a flask containing a suspension of 2,6-dimethyl-3-ethyl-4,4a,5,6,7,8,8a,9-octahydro-1H-pyrrolo[2,3-g]isoquinolin-4-one (0.984 g, 4.0 mmol) in ether (24 ml). Sodium metal (0.138 g, 6.0 mmol) was added and the solution stirred until all the sodium had dissolved. A solution of methyl iodide (1.28 g, 9.0 mmol) in ether (16 ml) was added and the mixture was stirred at room temperature until the ammonia evaporated. Water and chloroform were added and the aqueous layer was separated and extracted with chloroform. The combined extracts were washed with brine and dried over anhydrous sodium sulfate and concentrated to give 1.14 g. of crude product which was chromatographed on Alumina III to give 0.572 g. of white solid product. The chromatographed free base was converted to the hydrochloride salt with ethereal hydrogen chloride and crystallized from ethyl acetateethanol and ethanol to give pure 3-ethyl-1,2,6-trimethyl-4,4a,5,6,7,8,8a,9-octahydro-4a,-8a-trans-1H-pyrrolo[2,3-g]isoquinolin-4-one, hydrochloride (0.33 g, 28% yield) as white crystals, mp 241°–243°.

Anal. Calcd. for $C_{16}H_{24}N_2O \cdot HCl$: C, 64.74; H, 8.49; N, 9.44; $Cl^-$, 11.94; Found: C, 64.72; H, 8.63; N, 9.29; $Cl^-$, 12.03.

EXAMPLE 15

Preparation of
1-benzoyl-2,6-dimethyl-3-ethyl-4,4a,5,6,7,8,8a,9-octahydro-4a,8a-trans-1H-pyrrolo[2,3-g]isoquinolin-4-one To a suspension of 3-ethyl-2,6-dimethyl-4,4a,5,6,7,8,8a,9-octahydro-1H-pyrrolo-[2,3-g]isoquinolin-4-one (492.7 mg, 2.0 mmol) in dry tetrahydrofuran (10 ml) at −30° was added butyllithium (1.6 ml, 2.4 mmol, 1.5 M solution in hexane) over 2–3 minutes via syringe. The solution was stirred at −30° for 1 hour and benzoyl chloride (336 mg, 2.4 mmol) was added over 2–3 minutes. The resulting solution was stirred for 1 hour at −25° to −35° and for 0.5 hours at room temperature. The solution was poured into ice water (30 ml) and extracted with chloroform. The combined extracts were washed with brine and dried over anhydrous sodium sulfate. Evaporation of the solvent afforded the crude product (0.9 g), which was chromatographed (dry column, silica gel, eluting with a chloroform-aqueous methanol-acetic acid solution). Column fractions were treated with ammonium hydroxide and extracted with chloroform and washed with water and dried over anhydrous sodium sulfate. Evaporation of the solvent gave 1-benzoyl-2,6-dimethyl-3-ethyl-4,4a,5,6,7,8,8a,9-octahydro-4a,8a-trans-1H-pyrrolo[2,3-g]-isoquinolin-4-one as a solid which was recrystallized from cyclohexane to give the pure product, mp 144°–146°.

Anal. Calcd. for $C_{22}H_{26}N_2O_2$: C, 75.40; H, 7.48; N, 7.99; Found: C, 75.63; H, 7.79; N, 8.01.

Utilizing the procedure of Example 15, the following compounds were prepared. The isolated compounds are the 4a,8a-trans isomers.

From 2,6-dimethyl-3-ethyl-4,4a,5,6,7,8,8a,9-octahydro-1H-pyrrolo[2,3-g]isoquinolin-4-one and benzyl chloride, there was obtained 1-benzyl-2,6-dimethyl-3-ethyl-4,4a,5,6,7,8,8a,9-octahydro-1H-pyrrolo[2,3-g]isoquinolin-4-one.

From 2,6-dimethyl-3-ethyl-4,4a,5,6,7,8,8a,9-octahydro-1H-pyrrolo[2,3-g]isoquinolin-4-one and 1-trimethylacetyl chloride, there was obtained 2,6-dimethyl-3-ethyl-(2,2-dimethyl-1-oxopropyl)-4,4a,5,6,7,8,8a,9-octahydro-1H-pyrrolo[2,3-]isoquinolin-4-one, mp 110°–112°.

From 2-methyl-3-ethyl-6-(2-phenylethyl)-4,4a,5,6,7,8,8a,9-octahydro-1H-pyrrolo[2,3-g]isoquinolin-4-one and methyl iodide, there was obtained 3-ethyl-1,2-dimethyl-6-(2-phenylethyl)-4,4a,5,6,7,8,8a,9-octahydro-4a,8a-trans-1H-pyrrolo[2,3-g]isoquinolin-4-one, mp 180°–181° C.

EXAMPLE 16

Preparation of
3-ethyl-2-methyl-6-(2-propenyl)-4,4a,5,6,7,8,8a,9-octahydro-4a,8a-trans-1H-pyrrolo[2,3-g]isoquinolin-4-one A mixture of 3-ethyl-2-methyl-4,4a,5,6,7,8,8a,9-octahydro-1H-pyrrolo[2,3-g]isoquinolin-4-one (0.470 g, 2.03 mmol), allyl bromide (0.5 g, 4.13 mmol) and potassium carbonate (0.85 g, 6.16 mmol) in acetone (35 ml) was stirred at room temperature for 2 hours and was filtered. The filtrate was concentrated and the residue (0.53 g) chromatographed on Alumina III to give the product (0.40 g). This product was treated with ethereal hydrogen chloride to form the hydrochloride salt, which was recrystallized from ethanol-ethyl acetate to give 3-ethyl-2-methyl-6-(2-propenyl)-4,4a,5,6,7,8,8a,9-octahydro-4a,8a-trans-1H-pyrrolo[2,3-g]isoquinolin-4-one hydrochloride as a white solid, mp 214°–217°.

Anal. Calcd. for $C_{17}H_{24}N_2O \cdot HCl \cdot 0.5H_2O$ C, 64.24; H, 8.25; N, 8.81; $Cl^-$, 11.15; Found: C, 64.50; H, 8.48; N, 8.96; $Cl^-$, 11.37.

EXAMPLES 16a–dd

Following the procedure of Example 16, the compounds listed in Table II were prepared from the indicated 4,4a,5,6,7,8,8a,9-octahydro-1H-pyrrolo[2,3-g]-isoquinolin-4-one and the indicated halide. Each compound displayed spectral characteristics consistent with the described structure. Melting points are for the free base or hydrochloride salt (.HCl) as indicated. Compounds isolated are the 4a,8a-trans isomers.

TABLE II

Reaction scheme: starting material + R₄X → product (with K₂CO₃)

| Example | R₁ | R₂ | R₃ | R₄ | X | Analysis Calcd. | Analysis Found | mp | Crystallized from | Reaction conditions temp. | Reaction conditions time |
|---|---|---|---|---|---|---|---|---|---|---|---|
| 2-methyl-3-ethyl-6-(cyclopropylmethyl)-4,4a,5,6,7,8,8a,9-octahydro-1H-pyrrolo[2,3-g]isoquinolin-4-one, HCl, 0.2 molar hydrate 16a | H | CH₃ | CH₂CH₃ | cyclopropyl-CH₂ | Cl | (HCl) C 66.22 H 8.15 N 8.58 Cl⁻ 10.85 | C 66.24 H 8.35 N 8.36 Cl⁻ 10.51 | 215–9° | Ethanol ethyl acetate | reflux in acetone | 16 hours |
| 2-methyl-3-ethyl-6-benzyl-4,4a,5,6,7,8,8a,9-octahydro-1H-pyrrolo[2,3-g]isoquinolin-4-one HCl 16b | H | CH₃ | CH₂CH₃ | C₆H₅—CH₂ | Cl | (HCl) C 70.27 H 7.58 N 7.81 Cl⁻ 9.88 | C 70.49 H 7.33 N 7.72 Cl⁻ 10.03 | 193–7° | Ethanol | reflux in acetone | 2 hours |
| rac. 2-methyl-3-ethyl-6-[2-(dimethylamino)ethyl]-4,4a,5,6,7,8,8a,9-octahydro-4a,8a-trans-1H-pyrrolo[2,3-g]isoquinolin-4-one 16c | H | CH₃ | CH₂CH₃ | (CH₃)₂NCH₂CH₂ | Cl | C 71.25 H 9.63 N 13.85 | C 71.03 H 9.73 N 13.66 | 184–6° | ethyl acetate | reflux | 20 hours in 3-pentanone |
| rac. 2-methyl-3-ethyl-6-[4-(4-fluorophenyl)-4-oxobutyl]-4,4a,5,6,7,8,8a,9-octahydro-4a,8a-trans-1H-pyrrolo[2,3-g]isoquinolin-4-one 16d | H | CH₃ | CH₂CH₃ | F–C₆H₄–C(O)CH₂CH₂CH₂ | Cl | C 72.70 H 7.37 N 7.07 F 4.79 | C 72.47 H 7.47 N 7.09 F 4.75 | 210–12° | Ethyl acetate | reflux | 24 hours in 3-pentanone |
| rac. 2-methyl-3-ethyl-6-(2-phenylethyl)-4,4a,5,6,7,8,8a,9-octahydro-4a,8a-trans-1H-pyrrolo[2,3-g]isoquinolin-4-one 16e | H | CH₃ | CH₂CH₃ | C₆H₅–CH₂CH₂ | Br | C 78.53 H 8.39 N 8.33 | C 78.53 H 8.40 N 8.35 | 239–40° | ethyl acetate-ethanol | reflux | 2 hours in 3-pentanone |
| rac. 2-methyl-3-ethyl-6-(2-ethoxyethyl)-4,4a,5,6,7,8,8a,9-octahydro-4a,8a-trans-1H-pyrrolo[2,3-g]isoquinolin-4-one hydrochloride 16f | H | CH₃ | CH₂CH₃ | CH₃CH₂OCH₂CH₂ | Br | C 63.42 H 8.57 N 8.21 Cl⁻ 10.40 | C 63.13 H 8.71 N 8.17 Cl⁻ 10.64 | 213–5° | ethanol ethyl acetate | reflux | 2 hours in 3-pentanone |
| rac. 3,6-diethyl-2-methyl-4,4a,5,6,7,8,8a,9-octahydro-4a,8a-trans-H-pyrrolo- | H | CH₃ | CH₂CH₃ | CH₃CH₂ | Br | C 73.81 H 9.29 N 10.76 | C 73.91 H 9.30 N 10.84 | 228–30° | ethanol | reflux | 3 hours in acetone |

TABLE II-continued

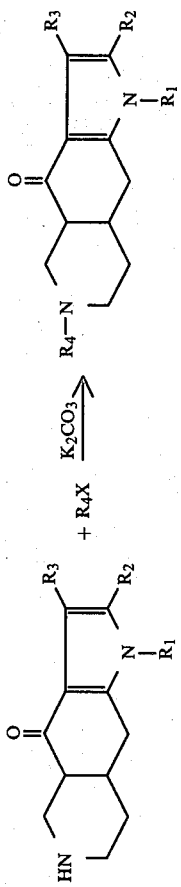

| Example | R$_1$ | R$_2$ | R$_3$ | R$_4$ | X | Analysis Calcd. | | Found | | mp | Crystallized from | temp. | Reaction conditions time |
|---|---|---|---|---|---|---|---|---|---|---|---|---|---|
| [2,3-g]isoquinolin-4-one 16h | | | | | | | | | | | | | |
| rac. 3-ethyl-2-methyl-6-propyl-4,4a,5,6,7,8,8a,9-octahydro-4a,8a-trans-1H-pyrrolo[2,3-g]isoquinolin-4-one 16i | H | CH$_3$ | CH$_2$CH$_3$ | CH$_3$CH$_2$CH$_2$ | Br | C H N | 74.41 9.55 10.21 | C H N | 74.29 9.40 10.21 | 226–8° | ethanol | reflux | 13 hours in 3-pentanone |
| 4a,8a-trans-3-ethyl-4-oxo-4a,5,6,7,8,8a,9-hexahydro-2-methyl-1H,4H-pyrrolo[2,3-g]isoquinoline-6-acetic acid ethyl ester 16j | H | CH$_3$ | CH$_2$CH$_3$ | CH$_3$CH$_2$OOCCH$_2$ | Br | C H N | 67.90 8.23 8.80 | C H N | 68.09 8.28 8.80 | 215–6° | ethanol-ethyl acetate | reflux | 2 hours in 3-pentanone |
| 4a,8a-trans-1-[3-ethyl-4a,5,6,7,8,8a,9-hexahydro-2-methyl-4-oxo-1H,4H-pyrrolo[2,3-g]isoquinolin-6-yl]-2-propanone 16k | H | CH$_3$ | CH$_2$CH$_3$ | H$_3$CCCH$_2$ ‖ O | Cl | C H N | 70.80 8.39 9.71 | C H N | 71.10 8.30 9.93 | 192–5° | ethanol | reflux | 2 hours in 3-pentanone |
| rac. 2-methyl-3-ethyl-6-[2-(4-fluorophenyl)-2-oxoethyl]-4,4a,5,6,7,8,8a,9-octahydro-4a,8a-trans-1H-pyrrolo[2,3-g]isoquinolin-4-one 16l | H | CH$_3$ | CH$_2$CH$_3$ | 4-F-C$_6$H$_4$-CO-CH$_2$ | Cl | C H N | 71.72 6.84 7.60 | C H N | 71.44 6.80 7.47 | 209–13° | ethanol | reflux | 3 hours in 3-pentanone |
| rac. 2-methyl-3-ethyl-6-[3-(4-fluorophenyl)-3-oxopropyl]-4,4a,5,6,7,8,8a,9-octahydro-4a,8a-trans-1H-pyrrolo[2,3-g]isoquinolin-4-one 16m | H | CH$_3$ | CH$_2$CH$_3$ | 4-F-C$_6$H$_4$-CO-CH$_2$CH$_2$ | Cl | C H N | 72.23 7.12 7.32 | C H N | 72.24 7.00 7.19 | 208–10° | ethanol | reflux | 3 hours in 3-pentanone |
| rac. 3-ethyl-2-methyl-6-(3-phenoxypropyl)-4,4a,5,6,7,8,8a,9-octahydro-1H-4a,8a-trans-pyrrolo[2,3-g]isoquinolin-4-one 16n | H | CH$_3$ | CH$_2$CH$_3$ | C$_6$H$_5$OCH$_2$CH$_2$CH$_2$ | Br | C H N | 75.37 8.24 7.64 | C H N | 75.64 8.18 7.52 | 202–3° | ethanol | reflux | 2 hours in 3-pentanone |

TABLE II-continued $$\text{HN} \underset{O}{\overset{R_3}{\diagdown}} \underset{N-R_1}{\overset{R_2}{\diagup}} + R_4X \xrightarrow{K_2CO_3} R_4-N \underset{O}{\overset{R_3}{\diagdown}} \underset{N-R_1}{\overset{R_2}{\diagup}}$$

| Example | R₁ | R₂ | R₃ | R₄ | X | Analysis Calcd. | | Found | mp | Crystallized from | Reaction conditions temp. | time |
|---|---|---|---|---|---|---|---|---|---|---|---|---|
| rac. 6-(3-diphenylpropyl)-3-ethyl-2-methyl-4,4a,5,6,7,8,8a,9-octahydro-4a,8a-trans-1H-pyrrolo[2,3-g]isoquinolin-4-one 16o | H | CH₃ | CH₂CH₃ | C₆H₅CHCH₂CH₂C₆H₅ | Cl | C 81.65 H 8.03 N 6.57 | | C 81.60 H 7.85 N 6.72 | 220-2° | | reflux | 17 hours in 3-pentanone |
| rac. 3-ethyl-6-[2-(4-methoxyphenyl)-ethyl]-2-methyl-4,4a,5,6,7,8,8a,9-octahydro-4a,8a-trans-1H-pyrrolo[2,3-g]isoquinolin-4-one 16p | H | CH₃ | CH₂CH₃ | CH₃O-C₆H₄-CH₂CH₂ | Cl | C 75.37 H 8.25 N 7.64 | | C 75.65 H 8.41 N 7.73 | 255-7° | ethanol | reflux | 24 hours in 3-pentanone |
| 3-ethyl-4,4a,5,6,7,8,8a,9-octahydro-2-methyl-6-[2-[tricyclo[3.3.1.1/3,7/]decan-1-yl]-2-oxoethyl]-4a,8a-trans-1H-pyrrolo[2,3-g]isoquinolin-4-one 16q | H | CH₃ | CH₂CH₃ | O=C-CH₂-(adamantyl) | Br | C 76.43 H 8.88 N 6.86 | | C 76.34 H 8.75 N 6.62 | 237-40° | ethanol | reflux | 3 hours in 3-pentanone |
| rac. 3-ethyl-2-methyl-6-(2-methylpropyl)-4,4a,5,6,7,8,8a,9-octahydro-4a,8a-trans-1H-pyrrolo[2,3-g]isoquinolin-4-one 16r | H | CH₃ | CH₂CH₃ | H₃C-CH-CH₂ with H₃C | Br | C 74.96 H 9.79 N 9.71 | | C 75.24 H 9.89 N 9.70 | 213-15° | ethanol | reflux | 10 hours in 3-pentanone |
| 16s rac. 3-ethyl-6-[2-(4-chlorophenyl)-ethyl]-2-methyl-4,4a,5,6,7,8,8a,9-octahydro-4a,8a-trans-1H-pyrrolo[2,3-g]isoquinolin-4-one | H | CH₃ | CH₂CH₃ | Cl-C₆H₄-CH₂CH₂ | Cl | C 71.24 H 7.34 N 7.55 | | C 71.25 H 7.16 N 7.63 | 264-7° | 1,4-dioxane | reflux | 20 hours in 3-pentanone |
| rac. 3-ethyl-6-[2-ethenyloxy)ethyl]-2-methyl-4,4a,5,6,7,8,8a,9-octahydro-4a,8a-trans-1H-pyrrolo[2,3-g]isoquinolin-4-one 16t | H | CH₃ | CH₂CH₃ | CH₂=CHOCH₂CH₂ | Cl | C 71.49 H 8.67 N 9.26 | | C 71.31 H 8.59 N 9.25 | 174-7° | acetonitrile | reflux | 10 hours in 3-pentanone |
| rac. 3-ethyl-2-methyl-6-(3-phenyl-2-propenyl)-4,4a,5,6,7,8,8a,9-octahydro-4a,8a-trans- | H | CH₃ | CH₂CH₃ | C₆H₅CH=CHCH₂ | Br | C 79.27 H 8.10 N 8.04 | | C 79.10 H 8.04 N 8.10 | 218-20° | ethanol | reflux | 4 hours in 3-pentanone |

TABLE II-continued

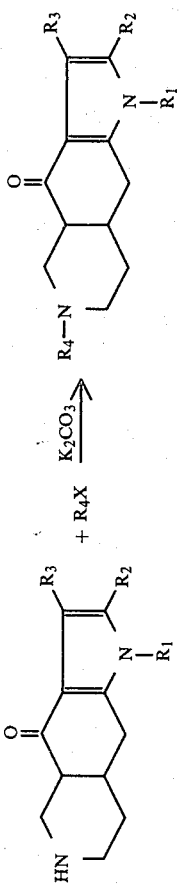

| Example | R₁ | R₂ | R₃ | R₄ | X | Analysis Calcd. | | Analysis Found | | mp | Crystallized from | Reaction conditions temp. | Reaction conditions time |
|---|---|---|---|---|---|---|---|---|---|---|---|---|---|
| 1H-pyrrolo[2,3-g]isoquinolin-4-one 16u | | | | | | | | | | | | | |
| 4a,8a-trans-3-ethyl-4a,5,7,8,-8a,9-hexahydro-2-methyl-4-oxo-1H,4H-pyrrolo[2,3-g]isoquinoline-6-propanoic acid ethyl ester 16v | H | CH₃ | CH₂CH₃ | CH₃CH₂OOCCH₂CH₂ | Br | C<br>H<br>N | 68.65<br>8.49<br>8.43 | C<br>H<br>N | 68.59<br>8.50<br>8.55 | 180-4° | acetonitrile | reflux | 3 hours in 3-pentanone |
| rac.-6-(cyclobutylmethyl)-3-ethyl-2-methyl-4a,4,5,6,7,8,8a,9-octahydro-4a,8a-trans-1H-pyrrolo[2,3-g]isoquinolin-4-one 16w | H | CH₃ | CH₂CH₃ | H₂C–CH₂–CHCH₂ (cyclobutylmethyl) | Cl | C<br>H<br>N | 75.96<br>9.39<br>9.32 | C<br>H<br>N | 75.70<br>9.34<br>9.23 | 222-4° | ethanol | reflux | 18 hours in 3-pentanone |
| rac.-6-(4-diphenylbutyl)-3-ethyl-2-methyl-4a,4,5,6,-7,8,8a,9-octahydro-4a,8a-trans-1H-pyrrolo[2,3-g]-isoquinolin-4-one 16x | H | CH₃ | CH₂CH₃ | C₆H₅CHCH₂CH₂CH₂C₆H₅ | Cl | C<br>H<br>N | 81.78<br>8.24<br>6.36 | C<br>H<br>N | 81.88<br>8.16<br>6.36 | 236-8° | ethanol | reflux | 18 hours in 3-pentanone |
| trans-[2-[3-ethyl-4,4a,5,6,-7,8,8a,9-octahydro-2-methyl-4-oxo-1H-pyrrolo[2,3-g]iso-quinolin-6-yl]ethyl]benzoic acid ester 16y | H | CH₃ | CH₂CH₃ | COOCH₂CH₂–C₆H₅ | Br | C<br>H<br>N | 72.60<br>7.42<br>7.36 | C<br>H<br>N | 72.31<br>7.58<br>7.22 | 206-8° | ethanol | reflux | 6 hours in 3-pentanone |
| rac. 3-ethyl-2-methyl-6-[2-(N-methyl-2-pyrrolidinyl)-ethyl]-4,4a,5,6,7,8,8a,9-octahydro-4a,8a-trans-1H-pyrrolo[2,3-g]isoquinolin-4-one 16z | H | CH₃ | CH₂CH₃ | N-methylpyrrolidinyl-CH₂CH₂ | Cl | C<br>H<br>N | 73.43<br>9.68<br>12.23 | C<br>H<br>N | 73.25<br>9.54<br>12.41 | 192-4° | ethyl acetate | reflux | 20 hours in 3-pentanone |
| trans-[3-[3-ethyl-4,4a,5,6-7,8,8a,9-octahydro-2-methyl-4-oxo-1H-pyrrolo[2,3-g]iso-quinolin-6-yl]propyl]benzoate 16aa | H | CH₃ | CH₂CH₃ | COOCH₂CH₂CH₂–C₆H₅ | Br | C<br>H<br>N | 73.07<br>7.67<br>7.10 | C<br>H<br>N | 73.12<br>7.63<br>7.07 | 189-90.5° | ethanol | reflux | 8 hours in 3-pentanone |

TABLE II-continued

[Reaction scheme: starting material with HN-CH₂ group and N-R₁, R₂, R₃ substituents + R₄X →(K₂CO₃) product with R₄-N replacing HN]

| Example | R₁ | R₂ | R₃ | R₄ | X | Analysis Calcd. | | Analysis Found | | mp | Crystallized from | Reaction conditions temp. | Reaction conditions time |
|---------|----|----|----|----|---|---|---|---|---|----|----|----|----|
| | | | | | | | | C | 66.32 | | | | |
| rac. 3-ethyl-2-methyl-6-(2,3-dihydroxypropyl)-4,4a,5,6,7,8,8a,9-octahydro-4a,8a-trans-1H-pyrrolo[2,3-g]isoquinolin-4-one 16bb | H | CH₃ | CH₂CH₃ | CH₂CH—CH₂ \| \| OH OH | Cl | C H N | 66.64 8.55 9.14 | C H N | 66.32 9.07 9.07 | 210–12° | ethanol | reflux | 20 hours in 3-pentanone |
| 3-ethyl-2-methyl-6-[(2,2-dimethyl-1,3-dioxolan-4-yl)methyl]-4,4a,5,6,7,8,8a,9-octahydro-4a,8a-trans-1H-pyrrolo[2,3-g]isoquinolin-4-one | H | CH₃ | CH₂CH₃ | CH₂—CH—CH₂ with O—C(CH₃)(CH₃)—O dioxolane | Br | C H N | 69.33 8.73 8.09 | C H N | 69.29 8.74 8.12 | 233–5° | ethanol | reflux | 20 hours in 3-pentanone |
| rac. 3-ethyl-6-[2-(4-morpholinyl)ethyl]-2-methyl-4,4a,5,6,7,8,8a,9-octahydro-4a,8a-trans-1H-pyrrolo[2,3-g]isoquinolin-4-one 16cc | H | CH₃ | CH₂CH₃ | morpholine-N—CH₂—CH₂ | Cl | C H N | 69.53 9.04 12.16 | C H N | 69.59 9.12 12.12 | 206–8° | ethanol | reflux | 8 hours in 3-pentanone |
| rac. 6-benzyl-2,3-dimethyl-4,4a,5,6,7,8,8a,9-octahydro-1H-4a,8a-trans-pyrrolo[2,3-g]isoquinolin-4-one 16dd | H | CH₃ | CH₃ | CH₂—C₆H₅ | Cl | C H N | 77.89 7.84 9.08 | C H N | 77.61 7.63 9.13 | 245.5–6° | ethanol | reflux | 3 hours in acetone |

EXAMPLE 17

Preparation of
3-ethyl-2-methyl-6-(2-hydroxy-2-phenylethyl)-
4,4a,5,6,7,8,8a,9-octahydro-4a,8a-trans-1H-pyrrolo[2,3-g]isoquinolin-4-one A mixture of 3-ethyl-2-methyl-4,4a,5,6,7,8,8a,9-octahydro-1H-pyrrolo[2,3-g]isoquinolin-4-one (0.83 g, 3.58 mmol) and styrene oxide (0.51 g, 4.22 mmol) in methanol (25 ml) was refluxed for 2.5 hours, cooled, and filtered. The filtrate was concentrated and the residue chromatographed on Alumina III to give 0.69 g. of crude product. Recrystallization from ethyl acetate-ethanol afforded 0.195 g. of 3-ethyl-2-methyl-6-(2-hydroxy-2-phenylethyl)-4,4a,5,6,7,8,8a,9-octahydro-4a,8a-trans-1H-pyrrolo[2,3-g]isoquinolin-4-one as a white solid, mp 218.5°–220°.

Anal. Calcd. for $C_{22}H_{28}N_2O_2$: C, 74.97; H, 8.01; N, 7.95; Found: C, 74.87; H, 7.92; N, 7.95.

EXAMPLES 17a–17f

Following the procedure of Example 17, the compounds listed in Table III were prepared from 3-ethyl-2-methyl-4,4a,5,6,7,8,8a,9-octahydro-1H-pyrrolo[2,3-g]isoquinolin-4-one and the indicated epoxide. Each compound displayed spectral characteristics consistent with the described structure. Melting points are for the free base or hydrochloride salt (.HCl) as indicated. The compounds isolated are the 4a,8a-trans isomers.

TABLE III

| Example | $R_1$ | $R_2$ | $R_3$ | $R_5$ | Analysis Calcd. | | Found | | mp | Crystallized from | Reaction Conditions temp. | time |
|---|---|---|---|---|---|---|---|---|---|---|---|---|
| 17a 2-methyl-3-ethyl-6-[2-hydroxy-2-(4-chlorophenyl)ethyl]-4,4a,5,6,7,8,8a,9-octahydro-1H-pyrrolo[2,3-g]isoquinolin-4-one | H | $CH_3$ | $CH_2CH_3$ | 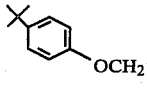 | C H N Cl | 68.29 7.03 7.24 9.16 | C H N Cl | 68.11 7.03 7.18 9.38 | 214–5° | Ethanol-ethyl acetate | reflux | 3 hours in methanol |
| 17b 2-methyl-3-ethyl-6-(2-hydroxyethyl)-4,4a,5,6,7,8,8a,9-octahydro-1H-pyrrolo-[2,3-g]isoquinolin-4-one | H | $CH_3$ | $CH_2CH_3$ | H | C H N | 69.53 8.75 10.14 | C H N | 68.93 8.78 9.96 | 215–8° | Ethanol | 25° | 2 hours in methanol |
| Ex.17c rac. 2-methyl-3-ethyl-6-[2-hydroxy-3-[4-(1,1-dimethylethyl)phenoxy]propyl]-4,4a,5,6,7,8,8a,9-octahydro-4a,8a-trans-1H-pyrrolo[2,3-g]isoquinolin-4-one | H | $CH_3$ | $CH_2CH_3$ | 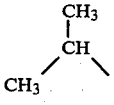 | C H N | 73.94 8.73 6.39 | C H N | 73.83 8.84 6.30 | 225–7° | ethyl acetate-ethanol | reflux | 2 hours in methanol |
| 17d rac. 2-methyl-3-ethyl-6-(2-hydroxy-3-methylbutyl)-4,4a,5,6,7,8,8a,9-octahydro-4a,8a-trans-1H-pyrrolo-[2,3-g]isoquinolin-4-one | H | $CH_3$ | $CH_2CH_3$ | $CH_3$-$CH$-$CH_3$ | C H N | 71.66 9.50 8.80 | C H N | 71.49 9.72 8.77 | 197–9° | ethanol-ethyl acetate | reflux | 5 hours in ethanol |
| 17e rac. 2-methyl-3-ethyl-6-(2-hydroxy-3,3-dimethylbutyl)-4,4a,5,6,7,8,8a,9-octahydro-4a,8a-trans-1H-pyrrolo-[2,3-g]isoquinolin-4-one | H | $CH_3$ | $CH_2CH_3$ | 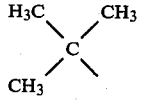 | C H N | 72.25 9.70 8.43 | C H N | 72.31 9.73 8.20 | 232–4° | ethanol-ethyl acetate | reflux | overnight in methanol |
| 17f rac. 2-methyl-3-ethyl-6-[2-hydroxy-3-(4-chlorophenoxy)propyl]-4,4a,5,6,7,8,8a,9-octahydro-4a,8a-trans-1H-pyrrolo[2,3-g]isoquinolin-4-one | H | $CH_3$ | $CH_2CH_3$ |  | C H N Cl | 66.26 7.01 6.72 8.50 | C H N Cl | 66.11 7.05 6.81 8.26 | 211–13° | ethanol | reflux | 3 hours in ethanol |

EXAMPLE 18

Resolution of racemic
3-ethyl-2,6-dimethyl-4,4a,5,6,7,8,8a,9-octahydro-4a,8a-trans-1H-pyrrolo[2,3-g]isoquinolin-4-one The racemic free base (prepared as in Example 4) (1.20 g.) was dissolved in methanol and a solution of d-(+)-tartaric acid (0.74 g.) in methanol was added. The solution was concentrated and recrystallized twice from methanol. The crystalline d-(+)-tartrate salt was treated with ammonium hydroxide to liberate the free base, and the free base was treated with anhydrous ethereal hydrogen chloride to give the hydrochloride salt. After two recrystallizations from ethanol and drying at 80°/0.005 mm, there was obtained 0.15 g. of the (−)-enantiomer as a white crystalline solid, mp 240°–245°.

rotation: $[\alpha]_D^{25}$ −120.78° (c 0.81%, water); Anal. Calcd. for $C_{15}H_{22}N_2O \cdot HCl \cdot 0.25H_2O$; C, 62.70; H, 8.24; N, 9.75; Found: C, 62.44; H, 8.33; N, 9.67.

The mother liquors from the crystallization of the d-(+)-tartrate salt were treated with ammonium hydroxide to liberate the free base which was treated with a solution of 1-(−)-tartaric acid (0.46 g.) in methanol. The solution was concentrated and recrystallized twice from methanol, converted to the free base and hydrochloride salt as described above to give 0.10 g. of the (+)-enantiomer as a white crystalline solid, mp 240°–244°.

rotation: $[\alpha]_D^{25}$ +121.38° (c 0.44%, water); Anal. Calcd. for $C_{15}H_{22}N_2O \cdot HCl \cdot 0.25H_2O$; C, 62.70; H, 8.24; N, 9.75; Found: C, 63.02; H, 8.20; N, 9.88.

EXAMPLE 19

N-[2-(3-ethyl-4,4a,5,6,7,8,8a,9-octahydro-2-methyl-4-oxo-4a,8a-trans-1H-pyrrolo[2,3-g]isoquinolin-6-yl)ethyl]-4-fluorobenzamide was prepared by heating 3-ethyl-2-methyl-4,4a,5,6,7,8,8a,9-octahydro-1H-pyrrolo[2,3-g]isoquinolin-4-one and 1-(4-fluorobenzoyl)-aziridine in a mixture of benzene and methanol for 2 hours. The crude product crystallized from ethanol as a white solid, mp 252°–253° C. The starting aziridine was prepared from aziridine and p-fluorobenzoyl chloride and sodium bicarbonate in water.

EXAMPLE 20

Preparation of 3-ethyl-2,6-dimethyl-4,4a,6,7,8,8a,9-octahydro-4a,8a-trans-1H-pyrrolo[2,3-g]isoquinolin-4-thione A mixture of 2.48 g. (0.01 mol) of 3-ethyl-2,6-dimethyl-4,4a,5,6,7,8,8a,9-octahydro-1H-pyrrolo[2,3-g]isoquinolin-4-one and 2.44 g. (0.008 mol) of $P_4S_{10}$ in 100 ml. of dioxane was stirred and refluxed for 17 hours. The dioxane was evaporated at reduced pressure and 150 ml. of water and enough ammonium hydroxide were added to bring the pH to 8–9. The mixture was extracted with chloroform and the extracts were washed with water and dried over sodium sulfate. Evaporation of the solvent gave the crude thione (3.3 g.) as a gummy material. Dry column chromatography gave 1.2 g. solid thione which was recrystallized twice from acetonitrile to give pure 3-ethyl-2,6-dimethyl-4,4a,5,6,7,8,8a,9-octahydro-4a,8a-trans-1H-pyrrolo[2,3-g]isoquinolin-4-thione, mp 194°–196° C. dec.

EXAMPLE 21

Preparation of 3-ethyl-2-methyl-4,4a,5,6,7,8,8a,9-octahydro-1H-pyrrolo[2,3-g]-isoquinolin-4-thione A mixture of 1.45 g. (6 mmol) of 3-ethyl-2-methyl-4,4a,5,6,7,8,8a,9-octahydro-1H-pyrrolo[2,3-g]isoquinolin-4-one and 1.77 g. (4 mmol) of phosphorus pentasulfide in 60 ml. of dioxane was stirred and refluxed for 10 hours. The mixture was cooled and the dioxane solution was decanted from a dark residue which was dissolved in 75 ml. of water. The solution was made alkaline (pH 8–9) with ammonium hydroxide and the aqueous mixture was extracted with chloroform. The extracts were washed with water and dried over sodium sulfate. Evaporation of the solvent gave 420 mg. of crude thione which was chromatographed (dry column, silica gel) together with 100 mg. of additional crude product obtained by hot water treatmentt of the residues from the initial isolation followed by the same chloroform extraction procedure. Elution of the dry column with the organic phase of a mixture prepared by equilibrating (by volume) 90 parts chloroform, 30 parts methanol, 10 parts water, and 6 parts acetic acid gave purified thione after evaporation, dissolution in water, neutralization to pH 8–9 with ammonium hydroxide, and extraction with chloroform. After washing with water, and drying over sodium sulfate, evaporation of the chloroform afforded 250 mg. of 3-ethyl-2-methyl-4,4a,5,6,7,8,8a,9-octahydro-1H-pyrrolo[2,3-g]isoquinolin-4-thione as a yellow solid, mp 190°–194°. Recrystallization from acetonitrile gave the pure 4a,8a-trans isomer, mp 203°–205°.

EXAMPLE 22

Preparation of 3-ethyl-2-methyl-6-(2-phenylethyl)-4,4a,5,6,7,8,8a,9-octahydro-4a,8a-trans-1H-pyrrolo[2,3-g]isoquinolin-4-thione A mixture of 248 mg. (1 mmol) of 3-ethyl-2-methyl-4,4a,5,6,7,8,8a,9-octahydro-1H-pyrrolo[2,3-g]isoquinolin-4-thione, 276 mg. of potassium carbonate, and 222 mg. of 2-bromoethylbenzene in 15 ml. of 3-pentanone was stirred and refluxed for 3 hours. The solvent was removed on a rotary evaporator, 25 ml. of water was added, and the mixture was extracted with chloroform. Purification by dry column chromatography as detailed in Example 21 gave 100 mg. of purified product, which gave 50 mg. of 3-ethyl-2-methyl-6-(2-phenylethyl)-4,4a,5,6,7,8,8a,9-octahydro-4a,8a-trans-1H-pyrrolo[2,3-g]isoquinolin-4-thione, mp 164°–166° C., dec., upon recrystallization from acetonitrile.

EXAMPLE 23

Capsule Formulation

| Ingredients | mg/capsule | | |
|---|---|---|---|
| | 0.5 | 5.0 | 10.0 |
| 3-ethyl-2,6-dimethyl-4,4a5,6,7,8,8a,9-octahydro-4a,8a-trans-1H-pyrrolo[2,3-g]isoquinolin-4-one hydrochloride | 0.5 | 5.0 | 10.0 |
| Lactose | 183.5 | 179.0 | 218.0 |
| Starch | 30.0 | 30.0 | 50.0 |
| Talc | 5.0 | 5.0 | 10.0 |
| Magnesium Stearate | 1.0 | 1.0 | 2.0 |
| Total | 220 mg. | 220 mg. | 290 mg. |

Procedure:
Mix the active ingredient, lactose and starch in a suitable mixer. Mill through a suitable mill. Mix with talc and magnesium stearate and fill on capsule machine.

EXAMPLE 24

Tablet Formulation (Direct Compression)

| Ingredients | mg/tablet | | |
|---|---|---|---|
| | 0.5 | 5.0 | 10.0 |
| 3-ethyl-2,6-dimethyl-4,4a,5,6,7,8,8a,9-octahydro-4a,8a-trans-1H-pyrrolo[2,3-g]isoquinolin-4-one, hydrochloride | 0.5 | 5.0 | 10.0 |
| Lactose | 85.5 | 81.0 | 103.0 |
| Avicel | 30.0 | 30.0 | 45.0 |
| Modified Starch | 7.5 | 7.5 | 10.0 |
| Magnesium Stearate | 1.5 | 1.5 | 2.0 |
| Total | 125 mg. | 125 mg. | 170 mg. |

-continued

| Ingredients | mg/tablet | | |
|---|---|---|---|
| | 0.5 | 5.0 | 10.0 |

Procedure:

Mix the active ingredient, lactose, avicel and modified starch in a suitable mixer for 10-15 minutes. Add the magnesium stearate as a premix and mix for 4 minutes. Compress on a suitable press.

EXAMPLE 25

Tablet Formulation (Wet Granulation)

| Ingredients | mg/tablet | | |
|---|---|---|---|
| | 0.5 | 5.0 | 10.0 |
| 3-ethyl-2,6-dimethyl-4,4a,5,6,7,8,8a,9-octahydro-4a,8a-trans-1H-pyrrolo[2,3-g]isoquinolin- | | | |

-continued

| Ingredients | mg/tablet | | |
|---|---|---|---|
| | 0.5 | 5.0 | 10.0 |
| 4-one, hydrochloride | 0.5 | 5.0 | 10.0 |
| Lactose | 103.5 | 99.0 | 148.0 |
| Modified Starch | 10.0 | 10.0 | 20.0 |
| Pregelatinized Starch | 10.0 | 10.0 | 20.0 |
| Magnesium Stearate | 1.0 | 1.0 | 2.0 |
| Total | 125 mg. | 125 mg. | 200 mg. |

Procedure:

Mix the active ingredient, lactose, modified starch and pregelatinized starch in a suitable mixer, granulate with water. Dry, mill. Mix with the magnesium stearate and compress on a suitable press.

We claim:
1. A compound of the formula:

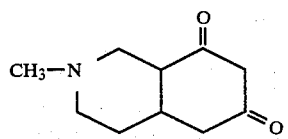

XII

* * * * *